US008483830B2

(12) United States Patent
Tweden et al.

(10) Patent No.: US 8,483,830 B2
(45) Date of Patent: Jul. 9, 2013

(54) METHODS AND SYSTEMS FOR GLUCOSE REGULATION

(75) Inventors: Katherine S. Tweden, Mahtomedi, MN (US); Mark B. Knudson, Shoreview, MN (US); Richard R. Wilson, Arden Hills, MN (US); Arnold W. Thornton, Roseville, MN (US); Dennis Dong-won Kim, La Jolla, CA (US)

(73) Assignee: EnteroMedics Inc., St. Paul, MN (US)

( * ) Notice: Subject to any disclaimer, the term of this patent is extended or adjusted under 35 U.S.C. 154(b) by 957 days.

(21) Appl. No.: 12/417,918

(22) Filed: Apr. 3, 2009

(65) Prior Publication Data

US 2009/0254143 A1    Oct. 8, 2009

Related U.S. Application Data

(60) Provisional application No. 61/042,575, filed on Apr. 8, 2008.

(51) Int. Cl.
*A61N 1/05* (2006.01)

(52) U.S. Cl.
USPC .............................. 607/40; 607/41; 607/133

(58) Field of Classification Search
USPC ............................................ 607/40, 41, 133
See application file for complete search history.

(56) References Cited

U.S. PATENT DOCUMENTS

| 5,231,988 | A | 8/1993 | Wernicke et al. |
| 6,832,114 | B1 | 12/2004 | Whitehurst et al. |
| 6,928,320 | B2 | 8/2005 | King |
| 7,149,574 | B2 | 12/2006 | Yun et al. |
| 7,167,750 | B2 | 1/2007 | Knudson et al. |
| 7,167,751 | B1 | 1/2007 | Whitehurst et al. |
| 7,444,183 | B2 | 10/2008 | Knudson et al. |
| 7,477,944 | B1 | 1/2009 | Whitehurst et al. |
| 7,489,969 | B2 | 2/2009 | Knudson et al. |
| 7,599,737 | B2 | 10/2009 | Yomtov et al. |

(Continued)

FOREIGN PATENT DOCUMENTS

| WO | WO 2006/023498 A1 | 3/2006 |
| WO | WO 2008/151059 A2 | 12/2008 |
| WO | WO 2009/131639 | 10/2009 |

OTHER PUBLICATIONS

Bernal-Mizrachi, C. et al., "An Afferent Vagal Nerve Pathway Links Hepatic PPARα Activation to Glucocorticoid-Induced Insulin Resistance and Hypertension," *Cell Metabolism*, vol. 5, pp. 91-102 (Feb. 2007).

(Continued)

*Primary Examiner* — Joseph Dietrich
(74) *Attorney, Agent, or Firm* — Merchant & Gould, P.C.

(57) ABSTRACT

Various methods and apparatus for treating a condition associated with impaired glucose regulation in a subject comprising in one embodiment, applying a neural conduction block to a target nerve at a blocking site with the neural conduction block selected to at least partially block nerve pulses. In another embodiment, combinations of down-regulating and or up-regulating with or without pharmaceutical agents are used to treat impaired glucose regulation. In other embodiments, up-regulation or down-regulation of various nerves, such as the vagus and its branches, and the splanchnic is used to modify the production of GLP-1 and GIP, thereby controlling glucose levels. In yet further embodiments, combinations of down-regulating and or up-regulating with or without pharmaceutical agents are used to modify the production of GLP-1 and GIP, to treat impaired glucose regulation.

38 Claims, 13 Drawing Sheets

U.S. PATENT DOCUMENTS

| | | | |
|---|---|---|---|
| 7,620,454 B2 | 11/2009 | Dinsmoor et al. | |
| 7,620,455 B2 | 11/2009 | Maschino | |
| 2004/0172085 A1 | 9/2004 | Knudson et al. | |
| 2004/0172086 A1 | 9/2004 | Knudson et al. | |
| 2004/0172088 A1 | 9/2004 | Knudson et al. | |
| 2004/0176812 A1 | 9/2004 | Knudson et al. | |
| 2005/0038484 A1 | 2/2005 | Knudson et al. | |
| 2005/0131485 A1 | 6/2005 | Knudson et al. | |
| 2006/0047325 A1* | 3/2006 | Thimineur et al. | 607/45 |
| 2006/0190053 A1 | 8/2006 | Dobak, III | |
| 2006/0229685 A1 | 10/2006 | Knudson et al. | |
| 2007/0027484 A1 | 2/2007 | Guzman et al. | |
| 2007/0135857 A1 | 6/2007 | Knudson et al. | |
| 2007/0179556 A1 | 8/2007 | Ben Haim et al. | |
| 2007/0203521 A1 | 8/2007 | Dobak et al. | |
| 2007/0225768 A1 | 9/2007 | Dobak, III | |
| 2008/0004672 A1 | 1/2008 | Dalal et al. | |
| 2008/0221644 A1 | 9/2008 | Vallapureddy et al. | |
| 2008/0281365 A1 | 11/2008 | Tweden et al. | |
| 2008/0300645 A1 | 12/2008 | Cholette | |
| 2008/0300646 A1 | 12/2008 | Cholette | |
| 2008/0300647 A1 | 12/2008 | Cholette | |
| 2008/0300648 A1 | 12/2008 | Cholette | |
| 2009/0254133 A1 | 10/2009 | Wendell | |
| 2009/0275997 A1 | 11/2009 | Faltys et al. | |
| 2009/0306465 A1 | 12/2009 | Dudai | |
| 2009/0306739 A1 | 12/2009 | Dilorenzo | |

OTHER PUBLICATIONS

Bloom, S. et al., "The release of pancreatic glucagon and inhibition of insulin in response to stimulation of the sympathetic innervation," *J. Physiol*, vol. 253, pp. 157-173 (1975).

Camilleri, M. et al., "Intra-abdominal vagal blocking (VBLOC therapy): Clinical results with a new implantable medical device," *Surgery*, vol. 143, No. 6, pp. 723-731 (Jun. 2008).

Camilleri, M. et al., "Selection of electrical algorithms to treat obesity with intermittent vagal block using an implantable medical device," *Surgery for Obesity and Related Diseases*, vol. 5, pp. 224-230 (2009).

Camilleri, M. et al., "Vagal Blocking for Obesity Control (Vbloc): Plasma Pancreatic Polypeptide (PPP) Response to a Standardized Sham Meal Challenge," *Obesity*, vol. 15, Supplement, Abstract No. 20-OR, pp. A6-A7 (Sep. 2007).

Dall, T. et al., "Economic Costs of Diabetes in the U.S. in 2007," *Diabetes Care*, vol. 31, No. 3, pp. 1-20 (Mar. 2008).

Frohman, L. et al., "Effect of Vagotomy and Vagal Stimulation on Insulin Secretion," *Diabetes*, vol. 16, No. 7, pp. 443-448 (Jul. 1967).

Gershon, "The Second Brain", Harper Collins Publishers, Inc., New York, NY, p. 19 (1998).

Görtz, L. et al., "A five- to eight-year follow-up study of truncal vagotomy as a treatment for morbid obesity," *Proceedings of the Third Annual Meeting American Society for Bariatric Surgery*, Iowa City, Iowa, p. 145 (Jun. 18-20, 1986).

Hardcastle, J. et al., "Effect of actively transported hexoses on afferent nerve discharge from rat small intestine," *J. Physiol.*, vol. 285, pp. 71-84 (1978).

Kahn, S. et al., "Glycemic Durability of Rosiglitazone, Metformin, or Glyburide Monotherapy," *The New England Journal of Medicine*, vol. 355, No. 23, pp. 2427-2443 (Dec. 7, 2006).

Kaneto, A. et al., "Effects of Stimulation of the Vagus Nerve on Insulin Secretion," *Endocrinology*, vol. 80, pp. 530-536 (Mar. 1967).

Knauf, C. et al., "Brain glucagon-like peptide-1 increases insulin secretion and muscle insulin resistance to favor hepatic glycogen storage," *The Journal of Clinical Investigation*, vol. 115, No. 12, pp. 3554-3563 (Dec. 2005).

Kow, L. et al., "Vagal blocking for obesity control (VBLOC): An open-label study of an implantable, programmable medical device to treat obesity," *Obesity Surgery*, vol. 17, Abstract No. 84, p. 1043 (2007).

Kral, J. et al., "Gastroplasty for Obesity: Long-Term Weight Loss Improved by Vagotomy", *World Journal of Surgery*, vol. 17, No. 1, pp. 75-79 (Jan./Feb. 1993).

Lim, G. et al., "Glucagon-Like Peptide 1 Secretion by the L Cell the View From Within," *Diabetes*, vol. 55, Suppl. 2, pp. S70-S77 (Dec. 2006).

Magee, D. et al., "Neural control of periodic secretion of the pancreas and the stomach in fasting dogs," *J. Physiol.*, vol. 344, pp. 153-160 (1983).

Matsuhisha, M. et al., "Important Role of the Hepatic Vagus Nerve in Glucose Uptake and Production by the Liver," *Metabolism*, vol. 49, No. 1, pp. 11-16 (Jan. 2000).

Mei, N. et al., "Nervous regulation of insulin release by the intestinal vagal glucoreceptors," *Journal of the Autonomic Nervous System*, vol. 4, pp. 351-363 (1981).

Mokdad, A. et al., "Prevalence of Obesity, Diabetes, and Obesity-Related Health Risk Factors, 2001," *JAMA*, vol. 289, No. 1, pp. 76-79 (Jan. 1, 2003).

Niijima, A., "Neural Mechanisms in the Control of Blood Glucose Concentration," *JN The Journal of Nutrition*, vol. 119, No. 6, pp. 833-840 (Jun. 1, 1989).

Oguma, Y. et al., "Weight Change and Risk of Developing Type 2 Diabetes," *Obesity Research*, vol. 13, No. 5, pp. 945-951 (May 2005).

Okosun, I. et al., "Hypertension and Type 2 Diabetes Comorbidity in Adults in the United States: Risk of Overall and Regional Adiposity," *Obesity Research*, vol. 9, No. 1, pp. 1-9 (Jan. 2001).

Peitl, B. et al., "The prandial insulin sensitivity-modifying effect of vagal stimulation in rats," *Metabolism Clinical and Experimental*, vol. 54, pp. 579-583 (2005).

Pories, W., "Diabetes the Evolution of a New Paradigm," *Annals of Surgery*, vol. 239, No. 1, pp. 12-13 (Jan. 2004).

Rocca, A. et al., "Role of the Vagus Nerve in Mediating Proximal Nutrient-Induced Glucagon-Like Peptide-1 Secretion," *Endocrinology*, vol. 140, No. 4, pp. 1687-1694 (1999).

Rozman, J. et al., "Stimulation of Nerves Innervating the Dog's Pancreas," *Artificial Organs*, vol. 26, No. 3, pp. 241-243 (2002).

Rubino, F., "Is Type 2 Diabetes an Operable Intestinal Disease?," *Diabetes Care*, vol. 31, Suppl. 2, pp. S290-S296 (Feb. 2008).

Rubino, F. et al., "Effect of Duodenal-Jejunal Exclusion in a Non-obese Animal Model of Type 2 Diabetes a New Perspective for an Old Disease," *Annals of Surgery*, vol. 239, No. 1, pp. 1-11 (Jan. 2004).

Solomonow, M. et al., "Control of muscle contractile force through indirect high-frequency stimulation," *American Journal of Physical Medicine*, vol. 62, No. 2, pp. 71-82 (1983).

Takahashi, T. et al., "Characterization of vagal pathways mediating gastric accommodation reflex in rats," *Journal of Physiology*, vol. 504, No. 2, pp. 479-488 (1997).

Taylor, I. et al., "Effect of Cephalic-Vagal Stimulation on Insulin, Gastric Inhibitory Polypeptide, and Pancreatic Polypeptide Release in Humans," *Journal of Clinical Endocrinology and Metabolism*, vol. 55, No. 6, pp. 1114-1117 (1982).

Toouli, J. et al., "Intra-Abdominal Vagal Blocking Reduces Calorie Intake, Enhances Satiation and Reduces Hunger During Significant and Sustained Weight Loss," *Gastroenterology*, vol. 134, No. 4, Suppl. 1, Abstract No. M1255, p. A-370, (Apr. 2008).

Toouli, J. et al., "Vagal blocking for obesity control (VBLOC): Effects on excess weight loss, calorie intake, satiation and satiety," *Obesity Surgery*, vol. 17, Abstract No. 83, p. 1043 (2007).

Tweden, K. et al., "Vagal Blocking for Obesity Control (VBLOC): Concordance of Effects of Very High Frequency Blocking Current at the Neural and Organ Levels Using Two Preclinical Models," *Gastroenterology*, vol. 130, No. 4, Suppl. 2, Abstract No. 951, p. A-148 (Apr. 2006).

Tweden, K. et al., "Vagal blocking for obesity control (VBLOC): Studies of pancreatic and gastric function and safety in a porcine model," *Surgery for Obesity and Related Diseases*, vol. 2, No. 3, Abstract No. 46, pp. 301-302 (May/Jun. 2006).

Uno, K. et al., "Neuronal Pathway from the Liver Modulates Energy Expenditure and Systemic Insulin Sensitivity," *Science*, vol. 312, pp. 1656-1659 (Jun. 16, 2006).

Williams, D. et al., "Vagotomy Dissociates Short- and Long-Term Controls of Circulating Ghrelin," *Endocrinology*, vol. 144, No. 12, pp. 5184-5187 (Dec. 2003).

Wilson, R. et al., "Intra-Abdominal Vagal Blocking Reduces Body Weight with Associated Reductions in Heart Rate and Without Adverse Effects on Electrocardiographic Parameters," *Obesity Surgery*, vol. 18, Abstract No. O53, p. 923 (2008).

Woods, S. et al., "Neural Control of the Endocrine Pancreas," *Physiological Reviews*, vol. 54, No. 3, pp. 596-619 (Jul. 1974).

Greenway et al., "Electrical Stimulation as Treatment for Obesity and Diabetes", Journal of Diabetes Science and Technology, vol. 1, Issue 2, Mar. 2007.

Herrera et al., *Obesity Surgery* 18:946 (2008).

Kow et al., *Obesity Surgery*, 18:924 (2008).

Tweden et al., *Obesity Surgery* (2006) 16:988.

Weiss, "Devices for the Treatment of Obesity: Will Understanding the Physiology of Satiety Unravel New Targets for Intervention?" J Diabetes Sci Technol, vol. 2, Issue 3, May 2008.

International Search Report and Written Opinion mailed Jul. 8, 2009.

Kow et al., Obesity Surgery, 18:914-915 (2008).

* cited by examiner

METHODS AND SYSTEMS FOR GLUCOSE REGULATION

CROSS-REFERENCE TO OTHER APPLICATIONS

This application claims the benefit of U.S. Ser. No. 61/042,575, filed Apr. 4, 2008, which application is incorporated by reference herein.

BACKGROUND OF THE INVENTION

An estimated 18.2 million people in the United States, 6.3 percent of the population, have diabetes, a serious, lifelong condition. The major forms of diabetes are Type 1 and Type 2. Type 1 diabetes is an autoimmune disease resulting in the destruction of the beta cells in the pancreas so that the pancreas then produces little or no insulin. A person who has Type 1 diabetes must take insulin daily to live. The most common form of diabetes is Type 2 diabetes. In the United States, about 10% of people aged 40 to 59 and 20% of the people 60 years of age and older have Type 2 diabetes. This disease is the 6$^{th}$ leading cause of death and contributes to development of heart disease, stroke, hypertension, kidney disease and nerve damage. Although several treatments are available for diabetes, about 15-32% of the patients fail to maintain glycemic control with monotherapy. (Kahn et al, NEJM 355:23 (2006)) Type 2 diabetes remains a significant health problem and has a cost to the health care system of at least 174 billion dollars. (Dall et al, Diabetes Care 31:1-20 (2008))

Type 2 diabetes is associated with older age, obesity, family history of diabetes, previous history of gestational diabetes, physical inactivity, and ethnicity. When Type 2 diabetes is diagnosed, the pancreas is usually producing enough insulin, but for unknown reasons, the body cannot use the insulin effectively, a condition called insulin resistance. After several years, insulin production decreases, and insulin must be administered orally or via injection to maintain glucose homeostasis, as in Type 1 diabetes.

In the early stages of Type 2 Diabetes, therapy consists of diet, exercise and weight loss, later to be followed by various drugs which can increase the output of the pancreas or decrease the requirement for insulin, and finally administration of insulin directly. Pharmaceuticals for treatment of diabetes are members of five classes of drugs: sulfonylureas, meglitinides, biguanides, thiazolidinediones, and alpha-glucosidase inhibitors. These five classes of drugs work in different ways to lower blood glucose levels. Some increase insulin output from the pancreas, some decrease glucose output by affecting liver function. Even with such treatment, some patients do not achieve glycemic control.

Exenatide is the first in a new class of drugs called incretin mimetics, for the treatment of Type 2 diabetes. Exenatide is a synthetic version of exendin-4, a naturally-occurring hormone that was first isolated from the saliva of the lizard known as a Gila monster. Exenatide works to lower blood glucose levels primarily by mimicking the action of GLP-1 to increase insulin secretion. Because it only has this effect in the presence of elevated blood glucose levels, it does not tend to increase the risk of hypoglycemia on its own, although hypoglycemia can occur if it is taken in conjunction with a sulfonylurea. The primary side effect is nausea, which tends to improve over time. Patients using exenatide have generally experienced modest weight loss as well as improved glycemic control.

More recently, a new class of medications called DPP-4 inhibitors has been developed which work by preventing the breakdown of a gut hormone, Glucagon-Like Peptide-1 (GLP-1). GLP-1 reduces blood glucose levels in the body, but has a half-life ~2 minutes, and therefore does not work well when injected as a drug itself. By interfering in the process that breaks down GLP-1, DPP-4 inhibitors allow it to remain active in the body longer, lowering blood glucose levels only when they are elevated. DPP-4 inhibitors do not tend to cause weight gain and tend to have a neutral or positive effect on cholesterol levels. Sitagliptin is currently the only DPP-4 inhibitor on the market.

A third category of therapy for Type 2 Diabetics has emerged in the last 10 years, and is increasing in popularity for certain patients. This involves gastric procedures such as various types of gastric bypass, and gastric restrictive techniques. Unexpectedly, these procedures have demonstrated resolution of Type 2 diabetics (for 75-85% of the patients), often within 2-3 days of the procedure, and independent of weight loss. Most patients have been morbidly obese (Body Mass Index, BMI>40), but evolving techniques are allowing the procedures to be applied to patients with BMI>35, and even over-weight or slightly obese patients. However, these surgical options are costly and have risks for the patient both before and after the surgery.

Methods of treating diabetes by upregulating neural activity have been described. Some of these methods for treating diabetes involve directly stimulating pancreatic cells, or parasympathetic/sympathetic tissue which directly innervates the pancreas. For example, U.S. Pat. No. 5,231,988 to Wernicke discloses application of a low frequency electrical signal to the vagus nerve to increase the secretion of endogenous insulin. U.S. Pat. No. 6,832,114 to Whitehurst describes the delivery of low frequency signals to at least one parasympathetic tissue innervating the pancreas to stimulate of pancreatic beta cells to increase insulin secretion. U.S. Pat. No. 7,167,751 to Whitehurst describes methods to relieve endocrine disorders by stimulating the vagus nerve.

Other studies indicate that the role of the vagus nerve with regard to regulation of insulin and blood glucose is not clear. A recent study suggests that damaging the afferent hepatic vagus nerve can inhibit the development of insulin resistance in mice treated with dexamethasone. (Bernal-Mizrachi et al., Cell Metabolism, 2007, 5:91). In rats, some studies indicate that vagotomy induces insulin resistance and in other studies, electrical stimulation induces insulin resistance. (Matsuhisa et al, Metabolism 49:11-16 (2000); Peitl et al., Metabolism 54:579 (2005)). In another mouse model, hepatic vagotomy suppressed increases in insulin sensitivity due to peroxisome proliferator-activated receptor expression. (Uno et al, 2006, Science 312:1656)

Despite the availability of many therapies, Type 2 diabetes remains a major health issue. Many of the therapies have undesirable side effects, do not achieve adequate glycemic control, or adequate glycemic control is not maintained. Thus, there remains a need to develop systems and methods for regulating glucose and/or treating diabetes.

SUMMARY

This disclosure describes methods and systems for treating impaired glucose regulation in a subject. A system comprises a programmable pulse generator (neuroregulator) with a lead and at least one electrode, the electrodes being placed on, or in close proximity to, target nerves or organs. In some embodiments, the system comprises at least two leads and the therapy is delivered across each electrode on the leads.

This disclosure is directed to methods and systems for treating a condition associated with impaired glucose regulation such as Type 2 diabetes, impaired glucose tolerance, and/or impaired fasting glucose. Patients having impaired glucose tolerance and/or impaired fasting glucose are also referred to as having prediabetes. In an embodiment, a method comprises treating a condition associated with impaired glucose regulation in a subject comprising: applying an intermittent neural signal to a target nerve at a site with said neural conduction signal selected to down-regulate or up-regulate afferent and/or efferent neural activity on the nerve and with neural activity restoring upon discontinuance of said signal. In some embodiments, the method further comprises administering a composition to the subject comprising an effective amount of an agent that improves glycemic control. In some embodiments, the agent stimulates insulin release, decreases hepatic glucose production, and/or increases insulin sensitivity. In some embodiments, patients are selected that have Type 2 diabetes. In other embodiments, subjects are patients having impaired glucose tolerance and/or impaired fasting glucose. In some cases, the combination of treatments may provide for a synergistic effect on Type 2 diabetes or and/or impaired glucose regulation and/or a decrease in the amount of the agent required to be effective, thereby minimizing side effects.

In embodiments, a method provides for treating a condition associated with impaired glucose regulation in a subject comprising: applying an intermittent electrical signal to a target nerve of the subject having impaired glucose regulation, with said electrical signal selected to down-regulate neural activity on the nerve and to restore neural activity on the nerve upon discontinuance of said signal. In embodiments, the electrical signal treatment is selected for frequency, and for on and off times. In some embodiments, the method further comprises applying an electrical signal treatment intermittently multiple times in a day and over multiple days to a second target nerve or organ, wherein the electrical signal has a frequency selected to upregulate and/or down-regulate activity on the target nerve and has an on time and an off time, wherein the off time is selected to allow at least a partial recovery of the activity of the target nerve. In some embodiments, the method further comprises administering a composition to the subject comprising an effective amount of an agent that improves glycemic control.

In yet other embodiments, methods are directed to modify the amount of GLP1, GIP, or both. In embodiments, a method of modifying the amount of GLP1, GIP, or both comprises: applying an first intermittent electrical signal to a target nerve, with said first electrical signal selected to down-regulate neural activity on the nerve and to restore neural activity on the nerve upon discontinuance of said signal, wherein the electrical signal is selected to modify the amount of GLP1, GIP, or both. In some embodiments, the method further comprises applying a second electrical signal treatment intermittently to a second target nerve or organ, wherein the second electrical signal has a frequency selected to upregulate activity on the target nerve or organ and to restore neural activity of the second target nerve or to restore activity of the target organ to baseline levels. In some embodiments, the method further comprises administering a composition to the subject comprising an effective amount of an agent that improves glycemic control.

In another aspect of the disclosure, a system for treating a patient with impaired glucose regulation is provided. In some embodiments, the system comprises: at least two electrodes operably connected to an implantable pulse generator, wherein one of the electrodes is adapted to be placed on a target nerve; an implantable pulse generator that comprises a power module and a programmable therapy delivery module, wherein the programmable therapy delivery module is configured to deliver at least one therapy program comprising an electrical signal treatment applied intermittently multiple times in a day and over multiple days to the target nerve, wherein the electrical signal has a frequency selected to downregulate activity on the target nerve and has an on time and an off time, wherein the off time is selected to allow at least a partial recovery of the activity of the target nerve; and an external component comprising an antenna and a programmable storage and communication module, wherein programmable storage and communication module is configured to store the at least one therapy program and to communicate the at least one therapy program to the implantable pulse generator. In some embodiments, the programmable therapy delivery module is configured to deliver a second therapy program comprising an electrical signal treatment applied intermittently multiple times in a day and over multiple days to a second target nerve or organ, wherein the electrical signal has a frequency selected to upregulate or down-regulate activity on the target nerve and has an on time and an off time, wherein the off time is selected to allow at least a partial recovery of the activity of the target nerve or organ.

DETAILED DESCRIPTION

Figure 1:
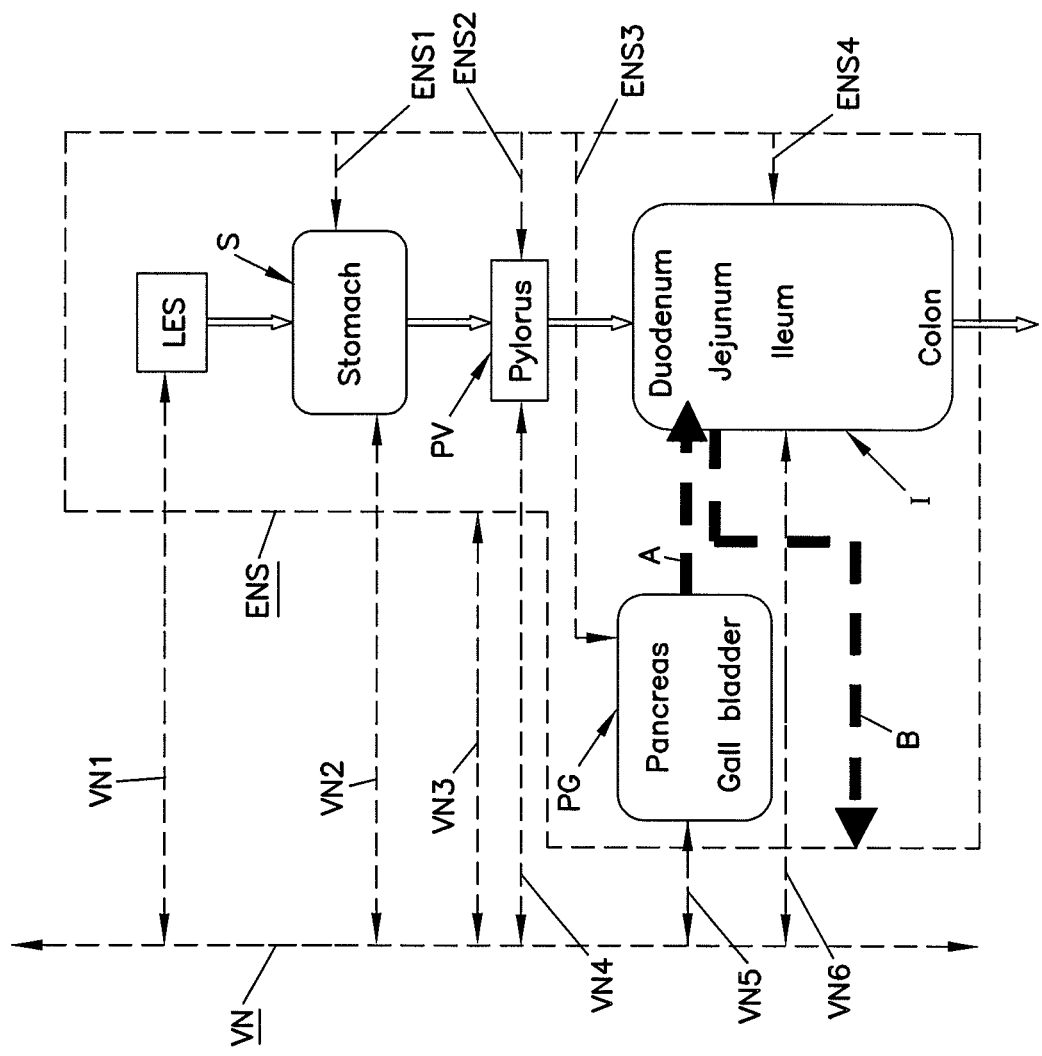
FIG. 1 is a schematic illustration of an alimentary tract (GI tract plus non-GI organs such as the pancreas and liver) and its relation to vagal and enteric enervation.

The following commonly assigned patent and U.S. patent applications are incorporated herein by reference: U.S. Pat. No. 7,167,750 to Knudson et al. issued Jan. 23, 2007; US 2005/0131485 A1 published Jun. 16, 2005, US 2005/0038484 A1 published Feb. 17, 2005, US 2004/0172088 A1 published Sep. 2, 2004, US 2004/0172085 A1 published Sep. 2, 2004, US 2004/0176812 A1 published Sep. 9, 2004 and US 2004/0172086 A1 published Sep. 2, 2004. Also incorporated herein by reference is International patent application Publication No. WO 2006/023498 A1 published Mar. 2, 2006.

This disclosure includes systems and methods for treating impaired glucose regulation in a subject. In embodiments, a method of treating a condition associated with impaired glucose regulation in a subject comprises applying an intermittent electrical signal to a target nerve of the subject, with said electrical signal selected to down-regulate neural activity on the nerve and to restore neural activity on the nerve upon discontinuance of said block. In some embodiments, the target nerve is the vagus nerve. In some embodiments, the site on the target nerve is located to avoid affecting heart rate such as below the vagal innervation of the heart. In some embodiments, the electrical signal is selected for frequency, amplitude, pulse width, and timing.

The electrical signal may also be further selected to improve glucose regulation. Improvement of glucose regulation can be determined by a change in any one of % of HbA1C, fasting glucose, or glucose tolerance. In some embodiments, the method further comprises combining the application of an electrical signal treatment with administration of an agent that affects glucose regulation. In some embodiments, the application of the electrical signal treatment excludes application of an electrical signal treatment to other nerves or organs.

As described in Example 1, application of an intermittent electrical signal treatment in patients provides for excess weight loss with no side effects on blood pressure or heart rate. In addition, application of the signal provides for a 30% decrease in calorie intake, an increase in satiation (feeling full), a decrease in satiety (hunger), and a decrease in pancreatic polypeptide. While not meant to limit the invention, it is expected that a decrease in calorie intake including a decrease in carbohydrates is expected to result in a decrease in glucose consumption. In addition, the decrease in pancreatic polypeptide indicates that pancreatic enzymes that participate in digestion will also be decreased thereby affecting the amount of glucose digested and absorbed into the system. Any effects of the electrical signal treatments as described herein on slowed gastric emptying would also contribute to a decrease in the amount and rate of glucose absorbed. A decrease in the amount and rate of blood glucose would lead to a decrease in the amount and rate of insulin production and/or administration required to control blood glucose.

Pharmaceutical treatments that delay gastric emptying and/or digestion of carbohydrates are known to lower postprandial blood glucose concentrations. Patients with delayed gastric emptying also have less postprandial glucose excursion. Thus, a treatment including downregulation of neural activity that results in a delay of gastric emptying and/or a decrease in carbohydrates consumed likely will result in lower blood glucose and enhance glucose regulation.

Other aspects of the methods and systems as described herein can influence the gut hormone balance to affect one or more of glucose absorption, insulin secretion, insulin sensitivity, and endogenous glucose production. Enteroendocrine-derived peptides modulate gastrointestinal motility and communicate signals regulating satiety to central nervous system centers, initiating and terminating food ingestion. Gut peptides, exemplified by glucagon-like peptide, regulate nutrient absorption and mucosal epithelial integrity, thereby optimizing nutrient absorption. At least 2 gastrointestinal peptides, glucagon-like peptide-1 (GLP-1) and glucose-dependent insulinotropic polypeptide (GIP), function as incretin hormones, potentiating insulin secretion in response to enteral nutrient signals.

In non-diabetics, when food enters the mouth, the pancreas initiates insulin secretion. As the food progresses into the duodenum, direct contact of the food with the wall of the duodenum produces secretion of the incretin hormone glucose-independent insulinotropic peptide (GIP), which among other functions, acts to increase secretion of insulin from the pancreas. GIP also promotes secretion of GLP-1 in the jejunum/ileum, which also acts to increase secretion of insulin from the pancreas. GLP-1 secretion in the distal jejunum/ileum shows a peak 15-30 minutes after food ingestion (GIP/neural pathway mediated), and a second peak 90-120 minutes after food ingestion (mediates by direct food contact with the jejunum/ileum). In Type 2 Diabetics, secretion of GIP is normal, but its effectiveness is reduced, while the secretion of GLP-1 is also reduced relative to normal. For Type 2 Diabetics, modulating the secretion of gut hormones, such as GLP-1, is way for providing glucose regulation. Other hormones may also be affected by the methods and systems as described herein including peptide YY, ghrelin, insulin, and glucagon.

In some aspects of the disclosure, a method and system comprises modulating the amount and/or secretion of a polypeptide such as glucagon-like peptide-1 (GLP-1), or glucose-dependent insulinotropic peptide (GIP) by application of a neural conduction block, or by application of neural stimulation, or a combination of both as described herein in order to facilitate glucose regulation. In other aspects of the disclosure, the methods and systems as described herein further comprise administration of an agent that affects glucose regulation including agents that affect gut hormones. Such administration of an agent can take place in the absence of, or in the presence of neural blocking and/or neurostimulation.

In some embodiments, a method and system comprises applying an intermittent electrical signal to a target nerve or organ of the subject, with said electrical signal selected to down-regulate neural activity on the nerve and to restore neural activity on the nerve upon discontinuance of said signal; and applying a second intermittent electrical signal to a second target nerve or organ of the subject, with said electrical signal selected to up-regulate or down-regulate neural activity on the nerve and to restore neural activity on the nerve upon discontinuance of said signal.

In embodiments, the first target nerve is selected from the group consisting of the anterior vagus nerve, the hepatic branch of the vagus nerve, the celiac branch of the vagus nerve, and the posterior vagus nerve. In embodiments, the second target nerve can include the celiac branch of the vagus nerve, nerves of the duodenum, jejunum, small bowel, colon and ileum, and sympathetic nerves enervating the gastrointestinal tract. In some embodiments, the first target organ can include the stomach, esophagus, and liver. In some embodiments, the second target organ can include the spleen, duodenum, small bowel, jejunum, colon, or ileum. In some embodiments, placement of an electrode on the pancreas is excluded.

In some embodiments a down regulating signal may be applied to a target nerve such as the anterior vagus nerve and the upregulating signal applied to a second target nerve such as the splanchnic or the celiac branch of the vagus nerve. In some embodiments, the upregulating signal can be applied to an electrode positioned on an organ such as spleen, duodenum, small bowel, jejunum, colon, or ileum and a downregulating signal applied to a vagus nerve. In some embodiments, the upregulating signal may be applied in response to detecting the presence of food in the duodenum or in response to an increase in blood glucose.

A. Description of Vagal Innervation of the Alimentary Tract

FIG. 1 is a schematic illustration of an alimentary tract (GI tract plus non-GI organs such as the pancreas and gall bladder (pancreas, liver, and gall bladder are considered GI organs), collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum). The biochemistry of the contents of the intestines I is influenced by the pancreas P and gall bladder PG which discharge into the duodenum. This discharge is illustrated by dotted arrow A.

Figure 2:
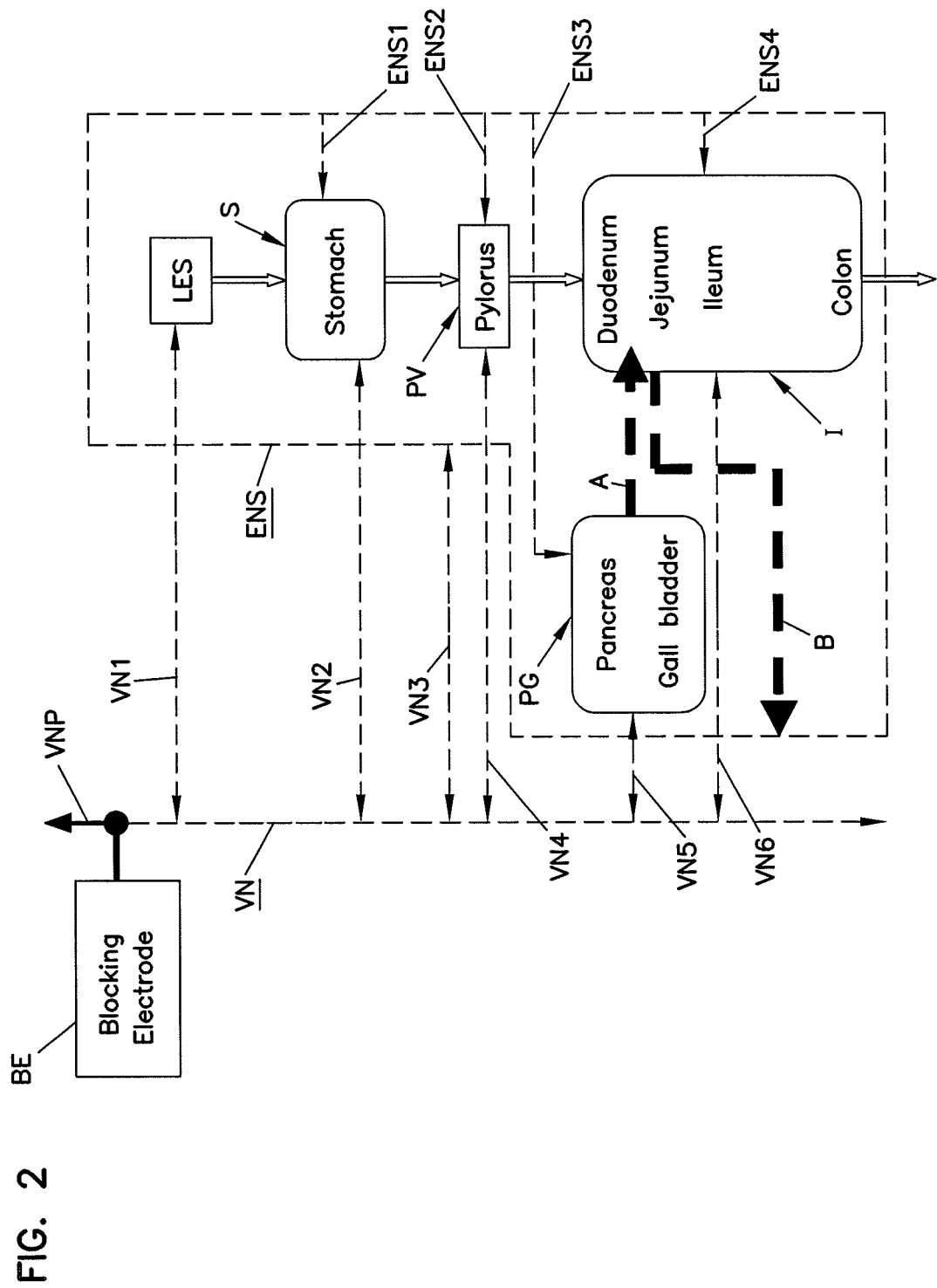
FIG. 2 is the view of FIG. 1 showing the application of a blocking electrode to the alimentary tract.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into anterior and posterior components with both acting to innervate the GI tract. In FIGS. 1, and 2, the anterior and posterior vagus nerves are not shown separately. Instead, the vagus nerve VN is shown schematically to include both anterior and posterior nerves. The vagus nerve VN contains both afferent and efferent components sending signals to and away from, respectively, its innervated organs.

The vagus nerve also includes the hepatic branch and the celiac nerve. The hepatic branch is involved in providing signals regarding glucose production in the liver. The celiac nerve or branch is formed by contributions from the greater splanchnic and vagus (especially the posterior or right vagus).

In addition to influence from the vagus nerve VN, the GI and alimentary tracts are greatly influenced by the enteric nervous system ENS. The enteric nervous system ENS is an interconnected network of nerves, receptors and actuators throughout the GI tract and pancreas and gall bladder PG. There are many millions of nerve endings of the enteric nervous system ENS in the tissues of the GI organs. For ease of illustration, the enteric nervous system ENS is illustrated as a line enveloping the organs innervated by the enteric nervous system ENS. The vagus nerve VN innervates, at least in part, the enteric nervous system ENS (schematically illustrated by vagal trunk VN3 which represents many vagus-ENS innervation throughout the gut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond to the biochemistry of the intestine contents (which are chemically modulated by the pancreao-biliary output of Arrow A). This biochemistry includes pH and osmolality.

In FIGS. 1 and 2, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—a historical procedure for treating ulcers), the enteric nervous system can operate the gut. Most enteric nerve cells are not directly innervated by the vagus. Gershon, "The Second Brain", Harper Collins Publishers, Inc, New York, N.Y. p. 19 (1998).

B. Therapy Delivery Equipment

The disclosure provides systems and devices for treating a condition associated with impaired glucose regulation comprising a pulse generator that provides signals to modulate neural activity on a target nerve or organ.

In embodiments, a system comprises at least two electrodes operably connected to an implantable pulse generator, wherein one of the electrodes is adapted to be placed on a target nerve; an implantable pulse generator that comprises a power module and a programmable therapy delivery module, wherein the programmable therapy delivery module is configured to deliver at least one therapy program comprising an electrical signal treatment applied intermittently multiple times in a day and over multiple days to the target nerve, wherein the electrical signal has a frequency selected to down-regulate and/or upregulate activity on the target nerve and has an on time and an off time, wherein the off time is selected to allow at least a partial recovery of the activity of the target nerve; and an external component comprising an antenna and a programmable storage and communication module, wherein programmable storage and communication module is configured to store the at least one therapy program and to communicate the at least one therapy program to the implantable pulse generator.

In an embodiment, a system (schematically shown in FIG. 3) for treating such conditions as diabetes or prediabetes includes a pulse generator 104, an external mobile charger 101, and two electrical lead assemblies 106, 106a. The pulse generator 104 is adapted for implantation within a patient to be treated. In some embodiments, the pulse generator 104 is implanted just beneath a skin layer 103.

In some embodiments, the lead assemblies 106, 106a are electrically connected to the circuitry of the pulse generator 104 by conductors 114, 114a. Industry standard connectors 122, 122a are provided for connecting the lead assemblies 106, 106a to the conductors 114, 114a. As a result, leads 116, 116a and the pulse generator 104 may be separately implanted. Also, following implantation, lead 116, 116a may be left in place while the originally placed pulse generator 104 is replaced by a different pulse generator.

The lead assemblies 106, 106a up-regulate and/or down-regulate nerves of a patient based on the therapy signals provided by the neuroregulator 104. In an embodiment, the lead assemblies 106, 106a include distal electrodes 212, 212a, which are placed on one or more nerves or organs of a patient. For example, the electrodes 212, 212a may be individually placed on the celiac nerve, the vagal nerve, the splanchnic nerve, or some combination of these, respectively, of a patient. For example, the leads 106, 106a have distal electrodes 212, 212a which are individually placed on the anterior and posterior vagal nerves AVN, PVN, respectively, of a patient, for example, just below the patient's diaphragm. Fewer or more electrodes can be placed on or near fewer or more nerves. In some embodiments, the electrodes are cuff electrodes.

The external mobile charger 101 includes circuitry for communicating with the implanted neuroregulator (pulse generator) 104. In some embodiments, the communication is a two-way radiofrequency (RF) signal path across the skin 103 as indicated by arrows A. Example communication signals transmitted between the external charger 101 and the neuroregulator 104 include treatment instructions, patient data, and other signals as will be described herein. Energy or power also can be transmitted from the external charger 101 to the neuroregulator 104 as will be described herein.

In the example shown, the external charger 101 can communicate with the implanted neuroregulator 104 via bidirectional telemetry (e.g. via radiofrequency (RF) signals). The external charger 101 shown in FIG. 3 includes a coil 102, which can send and receive RF signals. A similar coil 105 can be implanted within the patient and coupled to the neuroregulator 104. In an embodiment, the coil 105 is integral with the neuroregulator 104. The coil 105 serves to receive and transmit signals from and to the coil 102 of the external charger 101.

For example, the external charger 101 can encode the information as a bit stream by amplitude modulating or frequency modulating an RF carrier wave. The signals transmitted between the coils 102, 105 preferably have a carrier frequency of about 6.78 MHz. For example, during an information communication phase, the value of a parameter can be transmitted by toggling a rectification level between half-wave rectification and no rectification. In other embodiments, however, higher or lower carrier wave frequencies may be used.

In an embodiment, the neuroregulator 104 communicates with the external charger 101 using load shifting (e.g., modification of the load induced on the external charger 101). This change in the load can be sensed by the inductively coupled external charger 101. In other embodiments, however, the neuroregulator 104 and external charger 101 can communicate using other types of signals.

In an embodiment, the neuroregulator 104 receives power to generate the therapy signals from an implantable power source 151 such as a battery. In a preferred embodiment, the power source 151 is a rechargeable battery. In some embodiments, the power source 151 can provide power to the implanted neuroregulator 104 when the external charger 101 is not connected. In other embodiments, the external charger 101 also can be configured to provide for periodic recharging of the internal power source 151 of the neuroregulator 104. In an alternative embodiment, however, the neuroregulator 104 can entirely depend upon power received from an external source. For example, the external charger 101 can transmit power to the neuroregulator 104 via the RF link (e.g., between coils 102, 105).

In some embodiments, the neuroregulator 104 initiates the generation and transmission of therapy signals to the lead assemblies 106, 106a. In an embodiment, the neuroregulator 104 initiates therapy when powered by the internal battery 151. In other embodiments, however, the external charger 101 triggers the neuroregulator 104 to begin generating therapy signals. After receiving initiation signals from the external charger 101, the neuroregulator 104 generates the therapy signals (e.g., pacing signals) and transmits the therapy signals to the lead assemblies 106, 106a.

In other embodiments, the external charger 101 also can provide the instructions according to which the therapy signals are generated (e.g., pulse-width, amplitude, and other such parameters). In some embodiments, the external component comprises an antenna and a programmable storage and communication module. Instructions for one or more therapy programs can be stored in the programmable storage and communication module. In a preferred embodiment, the external charger 101 includes memory in which several predetermined programs/therapy schedules can be stored for transmission to the neuroregulator 104. The external charger 101 also can enable a user to select a program/therapy schedule stored in memory for transmission to the neuroregulator 104. In another embodiment, the external charger 101 can provide treatment instructions with each initiation signal.

Typically, each of the programs/therapy schedules stored on the external charger 101 can be adjusted by a physician to suit the individual needs of the patient. For example, a computing device (e.g., a notebook computer, a personal computer, etc.) 100 can be communicatively connected to the external charger 101. With such a connection established, a physician can use the computing device 107 to program therapies into the external charger 101 for either storage or transmission to the neuroregulator 104.

The neuroregulator 104 also may include memory in which treatment instructions and/or patient data can be stored. In some embodiments, the neuroregulator comprises a power module and a programmable therapy delivery module. For example, the neuroregulator 104 can store one or more therapy programs in the programmable therapy delivery module indicating what therapy should be delivered to the patient. The neuroregulator 104 also can store patient data indicating how the patient utilized the therapy system and/or reacted to the delivered therapy.

In some embodiments, the external component and/or the neuroregulator, are programmed with one or more therapy programs. One therapy program may comprise comprises an electrical signal treatment applied intermittently multiple times in a day and over multiple days, wherein the electrical signal has a frequency selected to downregulate activity on the target nerve and has an on time and an off time, wherein the off time is selected to allow at least a partial recovery of the activity of the target nerve. A second therapy program may comprise an electrical signal treatment applied intermittently multiple times in a day and over multiple days, wherein the electrical signal has a frequency selected to upregulate or down regulate activity on second target nerve or organ, and has an on time and an off time, wherein the off time is selected to allow at least a partial recovery of the activity of the target nerve. The first and/or second therapy programs may be applied at the same time, at different times, or at overlapping times. The first and/or second therapy programs may be delivered at specific times of the day, and or in response to a signal from a sensor.

Figure 3:
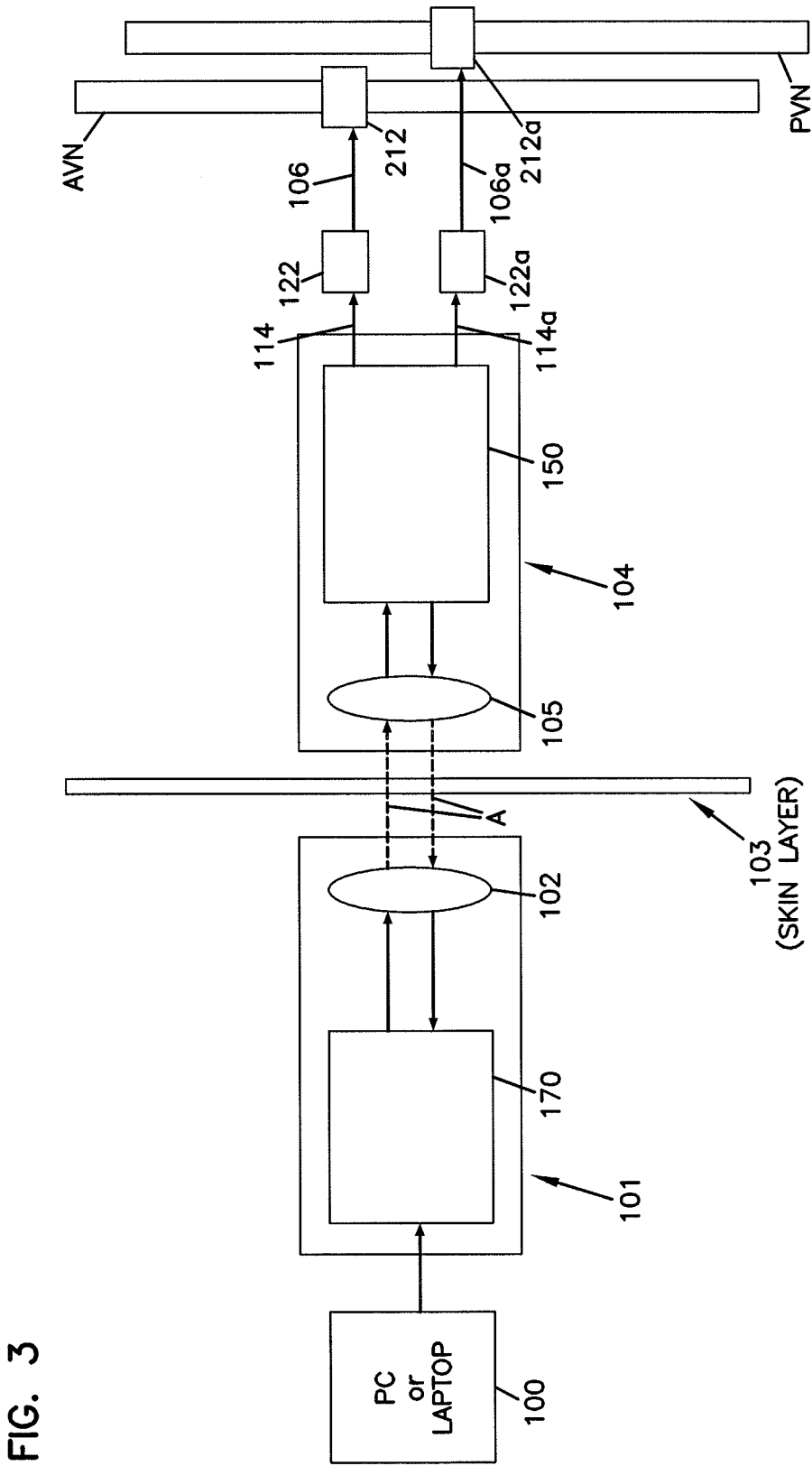
FIG. 3. is a schematic representation of an implantable system configuration for a gastro-intestinal treatment involving applying an electrical signal to a vagus nerve.

Referring to FIG. 3, the circuitry 170 of the external mobile charger 101 can be connected to an external coil 102. The coil 102 communicates with a similar coil 105 implanted within the patient and connected to the circuitry 150 of the pulse generator 104. Communication between the external mobile charger 101 and the pulse generator 104 includes transmission of pacing parameters and other signals as will be described.

Having been programmed by signals from the external mobile charger 101, the pulse generator 104 generates upregulating signals and/or downregulating signals to the leads 106, 106a. As will be described, the external mobile charger 101 may have additional functions in that it may provide for periodic recharging of batteries within the pulse generator 104, and also allow record keeping and monitoring.

While an implantable (rechargeable) power source for the pulse generator 104 is preferred, an alternative design could utilize an external source of power, the power being transmitted to an implanted module via the RF link (i.e., between coils 102, 105). In this alternative configuration, while powered externally, the source of the specific blocking signals could originate either in the external power source unit, or in the implanted module.

The electronic energization package may, if desired, be primarily external to the body. An RF power device can provide the necessary energy level. The implanted components could be limited to the lead/electrode assembly, a coil and a DC rectifier. With such an arrangement, pulses programmed with the desired parameters are transmitted through the skin with an RF carrier, and the signal is thereafter rectified to regenerate a pulsed signal for application as the stimulus to the vagus nerve to modulate vagal activity. This would virtually eliminate the need for battery changes.

However, the external transmitter must be carried on the person of the patient, which is inconvenient. Also, detection is more difficult with a simple rectification system, and greater power is required for activation than if the system were totally implanted. In any event, a totally implanted system is expected to exhibit a relatively long service lifetime, amounting potentially to several years, because of the relatively small power requirements for most treatment applications. Also, as noted earlier herein, it is possible, although considerably less desirable, to employ an external pulse generator with leads extending percutaneously to the implanted nerve electrode set. The major problem encountered with the latter technique is the potential for infection. Its advantage is that the patient can undergo a relatively simple procedure to allow short term tests to determine whether the condition associated with excess weight of this particular patient is amenable to successful treatment. If it is, a more permanent implant may be provided.

According to an embodiment of the present invention, an apparatus is disclosed for applying an electrical signal to an internal anatomical feature of a patient. The apparatus includes at least one electrode for implantation within the patient and placement at the anatomical feature (e.g., a nerve) for applying the signal to the feature upon application of the signal to the electrode. An implantable component is placed in the patient's body beneath a skin layer and having an implanted circuit connected to the electrode. The implanted circuit includes an implanted communication antenna. An external component has an external circuit with an external communication antenna for placement above the skin and adapted to be electrically coupled to the implanted antenna across the skin through radiofrequency transmission. The external circuit has a plurality of user interfaces including an information interface for providing information to a user and an input interface for receiving inputs from the user.

Figure 4:
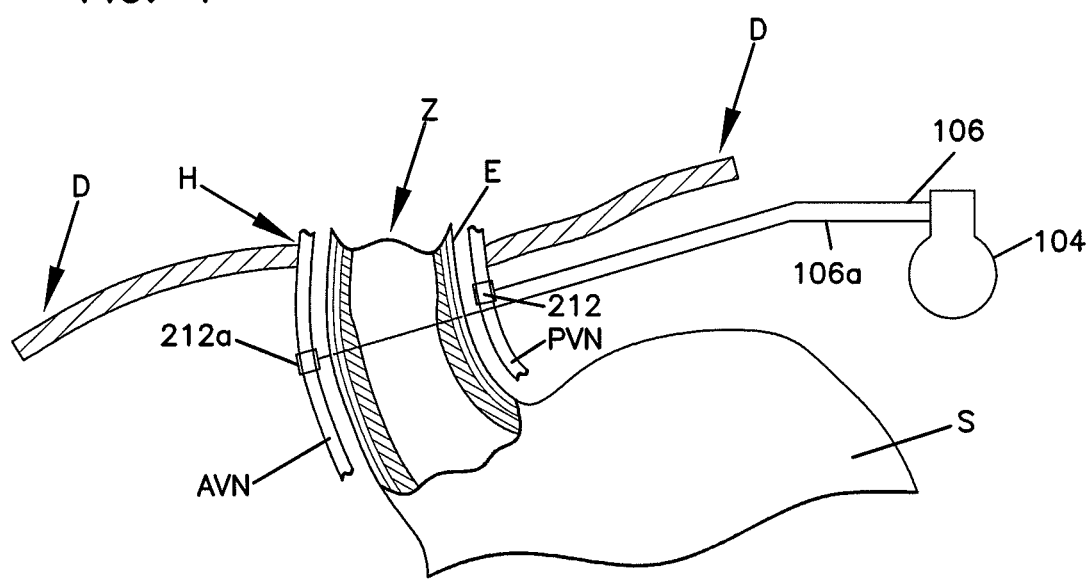
FIG. 4 is a schematic representation of an exemplary pulse generator (104) and leads (106) comprising electrodes 212 placed on an anterior and posterior vagus nerve.

With reference to FIG. 4, a device is shown for application of a signal to a nerve. A stomach S is shown schematically for the purpose of facilitating an understanding of applying a vagal nerve modulating signal. In FIG. 4, the stomach S is shown with a collapsed fundus F which is deflated due to fasting. In practice, the fundus F can be reduced in size and volume (as shown in FIG. 4) or expanded. The esophagus E passes through the diaphragm D at an opening or hiatus H. In the region where the esophagus E passes through the diaphragm D, trunks of the vagal nerve (illustrated as the anterior vagus nerve AVN and posterior vagus nerve PVN) are disposed on opposite sides of the esophagus E. It will be appreciated that the precise location of the anterior and posterior vagus nerves AVN, PVN relative to one another and to the esophagus E are subject to a wide degree of variation within a patient population. However, for most patients, the anterior and posterior vagus nerves AVN, PVN are in close proximity to the esophagus E at the hiatus H where the esophagus E passes through the diaphragm D.

The anterior and posterior vagus nerves AVN, PVN divide into a plurality of trunks that innervate the stomach directly and via the enteric nervous system and may include portions of the nerves which may proceed to other organs such as the pancreas, gallbladder and intestines. Commonly, the anterior and posterior vagus nerves AVN, PVN are still in close proximity to the esophagus E and stomach (and not yet extensively branched out) at the region of the junction of the esophagus E and stomach S.

In the region of the hiatus H, there is a transition from esophageal tissue to gastric tissue. This region is referred to as the Z-line (labeled "Z" in the Figures). Above the Z-line, the tissue of the esophagus is thin and fragile. Below the Z-line, the tissue of the esophagus E and stomach S are substantially thickened and more vascular. Within a patient population, the Z-line is in the general region of the lower esophageal sphincter. This location may be slightly above, slightly below or at the location of the hiatus H.

Figure 5:
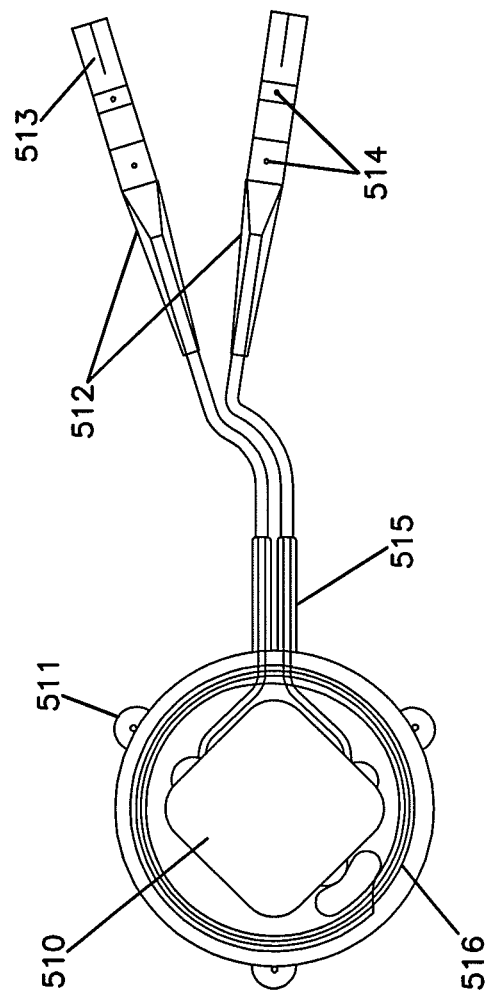
FIG. 5 illustrates a schematic representative of another exemplary embodiment comprising an implantable component comprising an electronic assembly 510 ("hybrid circuit") and a receiving coil 516; standard connectors 512 (e.g. IS-1 connectors) for attachment to electrode leads. Two leads are connected to the IS-1 connectors for connection to the implanted circuit. Both have a tip electrode for placement on a nerve. The patient receives an external controller comprising an antenna connected to control circuitry. The external control unit can be programmed for various signal parameters including options for frequency selection, pulse amplitude and duty cycle.

Another embodiment of a device useful in treating a condition associated with impaired glucose regulation as described herein is shown in FIG. 5. With reference to FIG. 5, a device comprises an implantable component comprising an electronic assembly 510 ("hybrid circuit") and a receiving coil 516; standard connectors 512 (e.g. IS-1 connectors) for attachment to electrode leads. Two leads are connected to the IS-1 connectors for connection to the implanted circuit. Both have a tip electrode for placement on a nerve. Set screws are shown in 514 and allow for adjustment of the placement of the electrodes. In some embodiments, a marker 513 to indicate the posterior or anterior lead is provided. Suture tabs 511 are provided to provide for implantation at a suitable site. In some embodiments, strain relief 515 is provided. The patient receives an external controller comprising an antenna connected to control circuitry. The external control unit can be programmed for various signal parameters including options for frequency selection, pulse amplitude and duty cycle.

In an embodiment, the nerves AVN, PVN are indirectly stimulated by passing electrical signals through the tissue surrounding the nerves. In some embodiments, the electrodes are bipolar pairs (ie. alternating anode and cathode electrodes). In some embodiments, a plurality of electrodes may be placed overlying the anterior and/or posterior vagus nerves AVN, PVN. As a result, energizing the plurality of electrodes will result in application of a signal to the anterior and posterior vagus nerves AVN, PVN and/or their branches. In some therapeutic applications, some of the electrodes may be connected to a blocking electrical signal source (with a blocking frequency and other parameters as described below) and other electrodes may apply an upregulating signal. Of course, only a single array of electrodes could be used with all electrodes connected to a blocking or a downregulating signal. In some therapeutic applications, some of the electrodes may be connected to an up-regulating electrical signal source (with a suitable frequency and other parameters as described below).

The electrical connection of the electrodes to an pulse generator may be as previously described by having a leads (eg. 106, 106a) connecting the electrodes directly to an implantable pulse generator (eg. 104). Alternatively and as previously described, electrodes may be connected to an implanted antenna for receiving a signal to energize the electrodes.

Two paired electrodes may connect to a pulse generator for bi-polar signal. In other embodiments, a portion of the vagus nerve VN is dissected away from the esophagus E. An electrode is placed between the nerve VN and the esophagus E. Another electrode is placed overlying the vagus nerve VN on a side of the nerve opposite the first electrode and with electrodes axially aligned (i.e., directly across from one another). Not shown for ease of illustration, the electrodes may be carried on a common carrier (e.g., a PTFE or silicone cuff) surrounding the nerve VN. Other possible placements of electrodes are described herein US 2005/0131485 published Jun. 16, 2005, which patent publication is hereby incorporated by reference.

While any of the foregoing electrodes could be flat metal pads (e.g., platinum), the electrodes can be configured for various purposes. In an embodiment, an electrode is carried on a patch. In other embodiments, the electrode is segmented into two portions both connected to a common lead and both connected to a common patch. In some embodiments, each electrode is connected to a lead and placed to deliver a therapy from one electrode to another. A flexible patch permits articulation of the portions of the electrodes to relieve stresses on the nerve VN.

Neuroregulator (Pulse Generator)

The neuroregulator (pulse generator) generates electrical signals in the form of electrical pulses according to a programmed regimen. In embodiments, a blocking signal is applied as described herein.

The pulse generator utilizes a conventional microprocessor and other standard electrical and electronic components, and communicates with an external programmer and/or monitor by asynchronous serial communication for controlling or indicating states of the device. Passwords, handshakes and parity checks are employed for data integrity. The pulse generator also includes means for conserving energy, which is important in any battery operated device and especially so where the device is implanted for medical treatment of a disorder, and means for providing various safety functions such as preventing accidental reset of the device.

Features may be incorporated into the pulse generator for purposes of the safety and comfort of the patient. In some embodiments, the patient's comfort would be enhanced by ramping the application of the signal up during the first two seconds. The device may also have a clamping circuit to limit the maximum voltage (14 volts for example) deliverable to the vagus nerve, to prevent nerve damage. An additional safety function may be provided by implementing the device to cease signal application in response to manual deactivation through techniques and means similar to those described above for manual activation. In this way, the patient may interrupt the signal application if for any reason it suddenly becomes intolerable.

The intermittent aspect of the electrical signal treatment resides in applying the signal according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective. In some embodiments, the predetermined on time and off time is programmed to allow for at least partial recovery of the nerve to a state of non down or up regulation.

Pulse generators, one supplying the right vagus and the other the left vagus to provide the bilateral upregulation and/or downregulation may be used. Use of implanted pulse generator for performing the method of the invention is preferred, but treatment may conceivably be administered using external equipment on an outpatient basis, albeit only somewhat less confining than complete hospitalization. Implantation of one or more pulse generators, of course, allows the patient to be completely ambulatory, so that normal daily routine activities including on the job performance is unaffected.

In some embodiments, signals can be applied at a portion of the nervous system remote from the vagus nerve such as at or near the stomach wall, for indirect regulation of the vagus nerve in the vicinity of the sub-diaphragmatic location. Here, at least one pulse generator is implanted together with one or more electrodes subsequently operatively coupled to the pulse generator via leads for generating and applying the electrical signal internally to a portion of the patient's nervous system to provide indirect blocking, down regulation, or upregulation of the vagus nerve in the vicinity of the desired location. Alternatively, the electrical signal may be applied non-invasively to a portion of the patient's nervous system for indirect application to a nerve or organ at a sub-diaphragmatic location.

The pulse generator may be programmed with programming wand and a personal computer using suitable programming software developed according to the programming needs and signal parameters which have been described herein. The intention, of course, is to permit noninvasive communication with the electronics package after the latter is implanted, for both monitoring and programming functions. Beyond the essential functions, the programming software should be structured to provide straightforward, menu-driven operation, HELP functions, prompts, and messages to facilitate simple and rapid programming while keeping the user fully informed of everything occurring at each step of a sequence. Programming capabilities should include capability to modify the electronics package's adjustable parameters, to test device diagnostics, and to store and retrieve telemetered data. It is desirable that when the implanted unit is interrogated, the present state of the adjustable parameters is displayed on the PC monitor so that the programmer may then conveniently change any or all of those parameters at the same time; and, if a particular parameter is selected for change, all permissible values for that parameter are displayed so that the programmer may select an appropriate desired value for entry into the pulse generator.

Other desirable features of appropriate software and related electronics would include the capability to store and retrieve historical data, including patient code, device serial number, number of hours of battery operation, number of hours of output, and number of magnetic activations (indicating patient intercession) for display on a screen with information showing date and time of the last one or more activations.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. However, battery life should considerably exceed that of other implantable medical devices, such as cardiac pacemakers, because of the relatively less frequent need for activation of the pulse generator of the present invention. In any event, the nerve electrodes are capable of indefinite use absent indication of a problem with them observed on the diagnostics testing.

The device may utilize circadian or other programming as well, so that activation occurs automatically at normal mealtimes for this patient. This may be in addition to the provision for the manual, periodic between meal, and sensing-triggered activation as described above herein.

The pulse generator may also be activated manually by the patient by any of various means by appropriate implementation of the device. These techniques include the patient's use of an external magnet, or of an external RF signal generator, or tapping on the surface overlying the pulse generator, to activate the pulse generator and thereby cause the application of the desired modulating signal to the electrodes. Another form of treatment of may be implemented by programming the pulse generator to periodically deliver the vagal activity modulation productive of glycemic control at programmed intervals.

In some embodiments, the system may include one or more sensors that may provide for signals to initiate therapy signals to one or more electrodes. For example, a sensor may measure the amount of glucose in the blood and initiate an upregulating signal to a nerve or organ in order to modify GLP1 production if the amount of glucose exceeds a certain threshold. In another embodiment, the sensor may measure strain or the presence of food entering the duodenum and apply an upregulating signal to the duodenum, small bowel, ileum, splanchnic nerve, or celiac branch of the vagus nerve.

C. Methods

The disclosure provides methods of treating a subject for a condition associated with impaired glucose regulation. In some embodiments, a method comprises: applying an intermittent electrical signal to a target nerve at a site with said electrical signal selected to down-regulate and/or up-regulate neural activity on the nerve and with normal or baseline neural activity restoring upon discontinuance of said block or up-regulation. In embodiments, the method provides for an increase in secretion of GIP and/or GLP-1. In some embodiments, the methods further comprise administering a composition to the subject comprising an effective amount of an agent that increases glycemic control. In some embodiments, the electrical signal is applied to the nerve by implanting a device or system as described herein.

In some embodiments, a method of treating a condition associated with impaired glucose regulation in a subject comprises applying an intermittent neural conduction block to a target nerve of the subject having impaired glucose regulation at a blocking site with said neural conduction block selected to down-regulate neural activity on the nerve and to restore neural activity on the nerve upon discontinuance of said block.

In other embodiments, methods include a diabetes or prediabetes treatment comprising selecting a drug for treating diabetes or impaired glucose control for a patient where effective dosages for treating diabetes or prediabetes for such a patient are associated with disagreeable side effects or impaired glycemic control; and treating a patient for diabetes or impaired glucose control with a concurrent treatment comprising: a) applying an intermittent neural block to a target nerve of the patient at multiple times per day and over multiple days with the block selected to down-regulate afferent and/or efferent neural activity on the nerve and with neural activity restoring upon discontinuance of said block; and b) administering said drug to the patient.

In other embodiments, a method of achieving glucose regulation in a patient comprises positioning an electrode on or near the vagus nerve, and an anodic electrode in contact with adjacent tissue; implanting a neurostimulator coupled to the electrodes into the patient, applying electrical pulses with defined characteristics of amplitude, pulse width, frequency and duty cycle to the vagus nerve wherein the defined characteristics are selected to improve glucose regulation in the patient.

In embodiments, the methods include a method of increasing or modifying the amount of GLP1, GIP, or both comprising: applying an intermittent electrical signal to a target nerve, with said electrical signal selected to up regulate or downregulate neural activity on the nerve and to restore neural activity on the nerve upon discontinuance of said signal, wherein the electrical signal is selected to modify the amount of GLP1, GIP, or both. In some embodiments, the electrical signal is selected for frequency, pulse width, amplitude and timing to downregulate neural activity as described herein. In some embodiments, the electrical signal is selected for frequency, pulse width, amplitude and timing to upregulate neural activity as described herein. In some embodiments, the electrical signal is selected to modify GLP1. In some embodiments, the electrical signal is selected to increase GLP1, especially when blood glucose is elevated.

In embodiments, the electrical signal is applied intermittently in a cycle including an on time of application of the signal followed by an off time during which the signal is not applied to the nerve, wherein the on and off times are applied multiple times per day over multiple days. In some embodiments, the on time is selected to have a duration of about 30 seconds to about 5 minutes. When the signal is selected to downregulate activity on the nerve, the electrical signal is applied at a frequency of about 200 Hz to 5000 Hz. When the signal is selected to upregulate activity on the nerve, the electrical signal is applied at a frequency of about 1 Hz to 200 Hz.

In embodiments, the electrical signal is applied to an electrode positioned on the vagus nerve. In some cases, the electrical signal is applied on the hepatic branch of the vagus nerve. In other cases, the electrical signal is applied on the celiac branch of the vagus nerve. In some embodiments, the e electrical signal is applied to an organ involved in glucose regulation such as the liver, duodenum, jejunum, or ileum.

In embodiments, downregulating and upregulating signals are both applied. In some cases, the signals are applied at the same time, different times, or overlapping times. In some embodiments, a downregulating signal is applied to a vagus nerve near the esophagus, and an upregulating signal applied to splanchnic nerve or the celiac branch of the vagus nerve. In some embodiments, a down regulating signal is applied to the vagus nerve near the esophagus and an upregulating signal is applied to the duodenum or ileum.

In embodiments, the method further comprises detecting the level of GLP1 or GIP to determine whether to apply an electrical signal treatment. If the levels of GLP1 and/or GIP are increased to normal or baseline levels expected in a control sample from a subject without diabetes, treatment to increase GLP1 and/of GIP may cease until the levels fall below the expected levels required to maintain adequate glucose control. Such levels are known or can be determined using methods known to those of skill in the art.

In embodiments, the method further comprises administering an agent that improves glucose control. Such agents include agents that increase the amount of insulin and/or increase the sensitivity of cells to insulin. Nonlimiting examples of agents include insulin, insulin analogs, sulfonylureas, meglitinides, GLP-1 analogs, DPP4 inhibitors, and PPAR alpha, gamma, or delta agonists.

Conditions Associated with Impaired Glucose Regulation

Conditions associated with impaired glucose regulation include Type 2 diabetes, impaired glucose tolerance, impaired fasting glucose, gestational diabetes, and Type 1 diabetes. "Impaired glucose regulation" refers to alterations in one or more of glucose absorption, glucose production, insulin secretion, insulin sensitivity, GLP-1 regulation, and glucagon regulation.

Type 2 diabetes is a disease in which liver, muscle and fat cells do not use insulin properly to import glucose into the cells and provide energy to the cells. As the cells begin to starve for energy, signals are sent to the pancreas to increase insulin production. In some cases, the pancreas eventually produces less insulin exacerbating the symptoms of high blood sugar. Patients with Type 2 diabetes have a fasting plasma glucose of 126 mg/dl or greater; oral glucose tolerance of 200 mg/dl or greater; and/or % of HbA1C of 6.5% or greater. In some cases, the HbA1C percentage is 6-7%, 7-8%, 8-9%, 9-10%, and greater than 10%.

Despite the presence of treatments for type 2 diabetes, not all patients achieve glucose control or maintain glucose control. A patient that has not achieved glycemic control will typically have an HbA1C of greater than 7%. In some embodiments, patients are selected that continue to have problems with glycemic control even with drug treatment.

Patients with impaired glucose tolerance and/or impaired fasting glucose are those patients that have evidence of some minimal level of lack of glucose control. Patients can be naïve to any treatment or are those that have been treated with one or more pharmaceutical treatments. "Pre-Diabetes" is a term that is used by the American Diabetes Association to refer to people who have a higher than normal blood glucose but not high enough to meet the criteria for diabetes. The lack of glycemic control can be determined by the fasting plasma glucose test (FPG) and/or the oral glucose tolerance test (OGTT). The blood glucose levels measured after these tests determine whether the patient has normal glucose metabolism, impaired glucose tolerance, impaired fasting glucose, or diabetes. If the patient's blood glucose level is abnormal within a specified range following the FPG, it is referred to as impaired fasting glucose (IFG); if the patient's glucose level is abnormal within a specified range following the OGTT, it is referred to as impaired glucose tolerance (IGT). A patient is identified as having impaired fasting glucose with a FPG of greater than equal to 100 to less than 126 mg/dl and/or impaired glucose tolerance with an OGTT of greater than or equal to 140 to less that 200 mg/dl. A person with Pre-Diabetes can have IFG and/or IGT in those ranges.

In some embodiments, patients are selected that are overweight but not obese (have a BMI less than 30) and have Type 2 diabetes, that are overweight but not obese and have pre-diabetes, or that have type 2 diabetes and are not overweight or obese. In some embodiments, patients are selected that have one or more risk factors for Type 2 diabetes. These risk factors include age over 30, family history, overweight, cardiovascular disease, hypertension, elevated triglycerides, history of gestational diabetes, IFG, and/or IGT.

In some embodiments, patients having impaired glucose regulation and that have gastroparesis may be excluded from the methods as described herein.

Signal Application

In one aspect of the disclosure a reversible intermittent modulating signal is applied to a target nerve or organ in order to downregulate and/or upregulate neural activity on the nerve.

In embodiments of the methods described herein a neural conduction block is applied to a target nerve at a site with said neural conduction block selected to down-regulate neural activity on the nerve and with neural activity restoring upon discontinuance of said signal. Systems for applying such a signal are been described U.S. Pat. No. 7,167,750; US2005/0038484 which is incorporated by reference.

In some cases, the nerve is a nerve that innervates one or more alimentary organs, including but not limited to the vagus nerve, celiac nerves, hepatic branch of the vagus nerve, and splanchnic nerve. The signal applied may upregulate and/or down regulate neural activity on one or more of the nerves.

In some embodiments, said modulating signal comprises applying an electrical signal. The signal is selected to down regulate or up regulate neural activity and allow for restoration of the neural activity upon discontinuance of the signal. A pulse generator, as described above, can be employed to regulate the application of the signal in order to alter the characteristic of the signal to provide a reversible intermittent signal. The characteristics of the signal include location of the signal, frequency of the signal, amplitude of the signal, pulse width of the signal, and the administration cycle of the signal. In some embodiments, the signal characteristics are selected to provide for improved glucose regulation.

In some embodiments, electrodes applied to a target nerve are energized with an intermittent blocking or down regulating signal. The signal is applied for a limited time (e.g., 5 minutes). The speed of neural activity recovery varies from subject to subject. However, 20 minutes is a reasonable example of the time needed to recover to baseline. After recovery, application of a blocking signal again down-regulates neural activity which can then recover after cessation of the signal. Renewed application of the signal can be applied before full recovery. For example, after a limited time period (e.g., 10 minutes) blocking can be renewed resulting in average neural activity not exceeding a level significantly reduced when compared to baseline. In some embodiments, the electrical signal is applied intermittently in a cycle including an on time of application of the signal followed by an off time during which the signal is not applied to the nerve, wherein the on and off times are applied multiple times per day over multiple days. In embodiments, the on and/or off times are selected to allow at least partial recovery of the nerve. While not meant to limit the disclosure, it is believed that allowing a recovery period for the nerve may avoid enteric accommodation.

Figure 6:
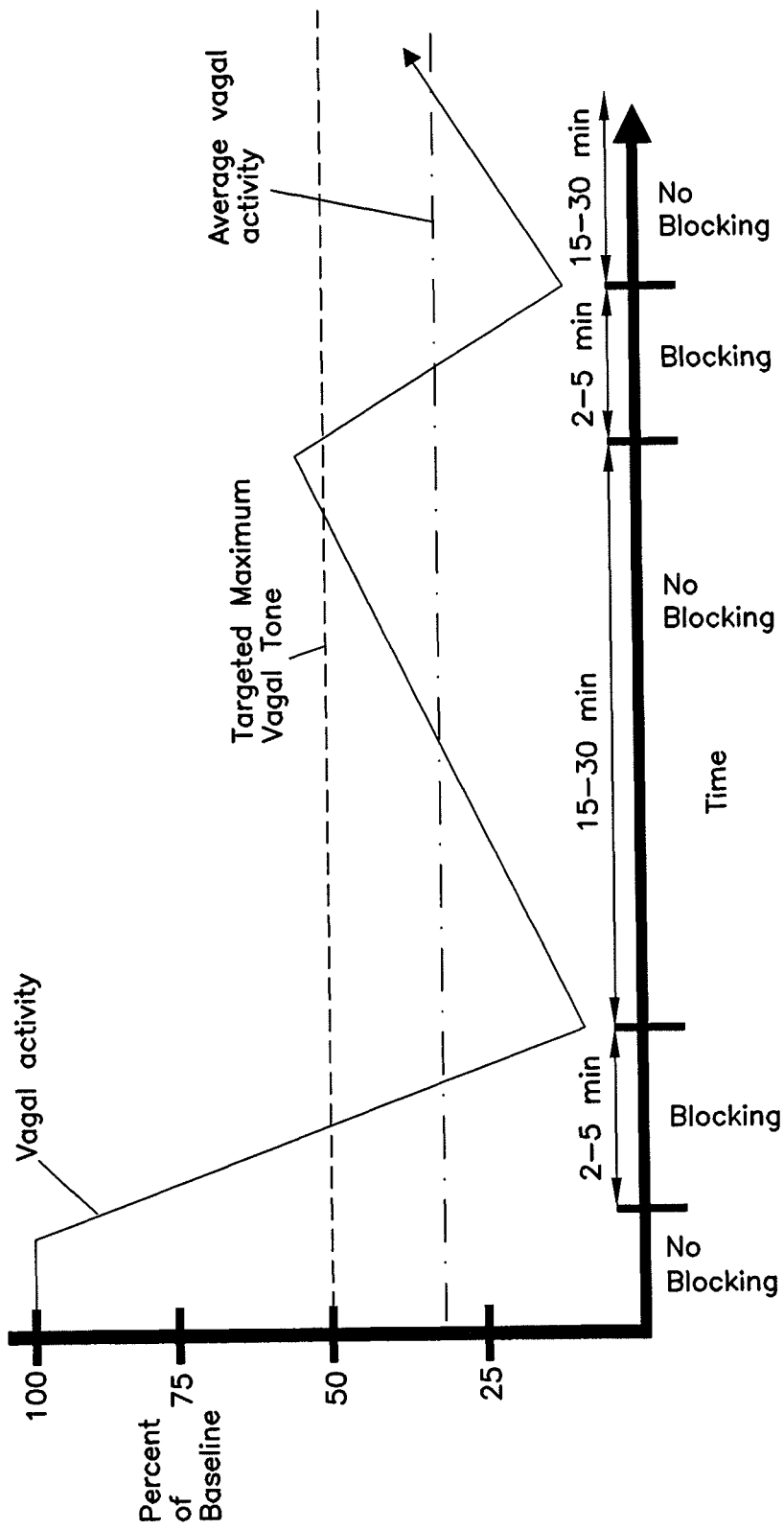
FIG. 6 shows recovery of the vagal nerve after application of blocking signal.

Recognition of recovery of neural activity, such as vagal activity, permits a treatment therapy and apparatus with enhanced control and enhanced treatment options. FIG. 6 illustrates vagal activity over time in response to application of a blocking signal as described above and further illustrates recovery of vagal activity following cessation of the blocking signal. It will be appreciated that the graph of FIG. 6 is illustrative only. It is expected there will be significant patient-to-patient variability. For example, some patients' responses to a blocking signal may not be as dramatic as illustrated. Others may experience recovery slopes steeper or shallower than illustrated. Also, vagal activity in some subjects may remain flat at a reduced level before increasing toward baseline activity. However, based on the afore-mentioned animal experiments, FIG. 6 is believed to be a fair presentation of a physiologic response to blocking.

In FIG. 6, vagal activity is illustrated as a percent of baseline (i.e., vagal activity without the treatment of the present invention). Vagal activity can be measured in any number of ways. For example, quantities of pancreatic exocrine secretion produced per unit time are an indirect measurement of such activity. Also, activity can be measured directly by monitoring electrodes on or near the vagus. Such activity can also be ascertained qualitatively (e.g., by a patient's sensation of bloated feelings or normalcy of gastrointestinal motility).

In FIG. 6, the vertical axis is a hypothetical patient's vagal activity as a percent of the patient's baseline activity (which varies from patient to patient). The horizontal axis represents the passage of time and presents illustrative intervals when the patient is either receiving a blocking signal as described or the blocking signal is turned off (labeled "No Blocking"). As shown in FIG. 6, during a short period of receiving the blocking signal, the vagal activity drops dramatically (in the example shown, to about 10% of baseline activity). After cessation of the blocking signal, the vagal activity begins to rise toward baseline (the slope of the rise will vary from patient to patient). The vagal activity can be permitted to return to baseline or, as illustrated in FIG. 6, the blocking signal can be re-instituted when the vagal activity is still reduced. In FIG. 6, the blocking signal begins when the vagal activity increases to about 50% of baseline. As a consequence, the average vagal activity is reduced to about 30% of the baseline activity. It will be appreciated that by varying the blocking time duration and the "no blocking" time duration, the average vagal activity can be greatly varied.

The signal may be intermittent or continuous. The preferred nerve conduction block is an electronic block created by a signal at the vagus by an electrode controlled by the implantable pulse generator (such as pulse generator 104 or an external controller). The nerve conduction block can be any reversible block. For example, ultrasound, cryogenics (either chemically or electronically induced) or drug blocks can be used. An electronic cryogenic block may be a Peltier solid-state device which cools in response to a current and may be electrically controlled to regulate cooling. Drug blocks may include a pump-controlled subcutaneous drug delivery.

With such an electrode conduction block, the block parameters (signal type and timing) can be altered by pulse regulator and can be coordinated with the upregulating signals. For example, the nerve conduction block is preferably within the parameters disclosed in Solomonow, et al., "Control of Muscle Contractile Force through Indirect High-Frequency Stimulation", Am. J. of Physical Medicine, Vol. 62, No. 2, pp. 71-82 (1983). In some embodiments, the nerve conduction block is applied with electrical signal selected to block the entire cross-section of the nerve (e.g., both afferent, efferent, myelinated and nomnyelinated fibers) at the site of applying the blocking signal (as opposed to selected sub-groups of nerve fibers or just efferent and not afferent or visa versa) and, more preferably, has a frequency selected to exceed the 200 Hz threshold frequency described in Solomonow et al. Further, more preferred parameters are a frequency of 500 Hz (with other parameters, as non-limiting examples, being amplitude of 4 mA, pulse width of 0.5 msec, and duty cycle of 5 minutes on and 10 minutes off). As will be more fully described, the present invention gives a physician great latitude in selecting stimulating and blocking parameters for individual patients.

In embodiments of the methods described herein a signal is applied to a target nerve at a site with said signal selected to up-regulate neural activity on the nerve and with neural activity restoring upon discontinuance of said signal. In some embodiments, an upregulating signal may be applied in combination with a down regulating signal in order to improve glucose regulation. For example, the upregulating signal may be applied to splanchnic nerve and/or celiac nerve.

The signal is selected to upregulate neural activity and allow for restoration of the neural activity upon discontinuance of the signal. A pulse generator, as described above, is employed to regulate the application of the signal in order to alter the characteristic of the signal to provide a reversible intermittent signal. The characteristics of the signal include frequency of the signal, location of the signal, and the administration cycle of the signal.

In some embodiments, electrodes applied to a target nerve are energized with an up regulating signal. The signal is applied for a limited time (e.g., 5 minutes). The speed of neural activity recovery varies from subject to subject. However, 20 minutes is a reasonable example of the time needed to recover to baseline. After recovery, application of an up signal again up-regulates neural activity which can then recover after cessation of the signal. Renewed application of the signal can be applied before full recovery. For example, after a limited time period (e.g., 10 minutes) upregulating signal can be renewed.

In some embodiments, an upregulating signal may be applied in combination with a down regulating signal in order to improve glucose regulation, decrease the amount of calories ingested or the amount of glucose absorbed from food, increase/modify the amount and/or secretion of GIP and/or GLP1, and/or decrease the amount of ghrelin secreted. The neural regulation signals can influence the amount of glucose produced by the liver, the amount of glucose absorbed from food, and the amount of GIP, GLP-1 and/or ghrelin secreted. The neural regulation provides for a decrease in the amount of insulin required by the subject.

The up-regulating and down-regulating signals may be applied to different nerves at the same time, applied to the same nerve at different times, or applied to different nerves at different times. In embodiments, an up-regulating signal may be applied to a celiac nerve or splanchnic nerve. In other embodiments, an up-regulating or downregulating signal may be applied to a hepatic branch of the vagus nerve or the signal may be applied to decrease the amount of hepatic glucose produced, especially in the early morning.

In some embodiments, a downregulating signal is applied to a vagus nerve branch intermittently multiple times in a day and over multiple days in combination with an upregulating signal applied intermittently multiple times in a day and over multiple days to a different nerve or organ. In some embodiments, the upregulating signal is applied due to a sensed event such as the amount of blood glucose present or the entry of food into the duodenum. In other embodiments, an upregulating signal applied to the splanchnic nerve, the celiac nerve, the duodenum and/or the ileum can be applied during a time period after normal meal times for the subject typically 15 to 30 minutes after mealtimes or times when glucose levels rise.

In some cases, signals are applied at specific times. For example, a downregulating signal may be applied before and during meal, followed by a stimulatory signal about 30 to 90 minutes after eating. In another example, a downregulating signal may be applied to the vagus nerve or the hepatic branch of the vagus nerve early in the morning when hepatic glucose is increasing.

In some embodiments, the signal parameters are adjusted to obtain an improvement in glucose regulation. An improvement, in glucose regulation can be determined by measurement of fasting glucose, oral glucose tolerance test, and/or the HbA1C or a decrease in the amount of insulin needed by the subject. In an embodiment, it is preferred that a reduction of the HbA1C in absolute percentage is at least 0.4% and more preferably is any % in the range of 0.4% to 5%. In some embodiments, a reduction of the HbA1C in absolute percentage is any one of 0.5%, 1%, 1.5%, 2%, 2.5%, 3%, 3.5%, 4%, 4.5%, or 5% or more. For example, a Type 2 diabetes patient may have a HbA1C of 9% and a reduction to HbA1C of 6.5% would be a reduction of 2.5% and would represent an improvement in glucose regulation.

In some embodiments, an improvement in glucose regulation comprises a fasting glucose of less than 126 mg/dl or greater and/or oral glucose tolerance of less than 200 mg/dl. In some embodiments the fasting glucose and/or oral glucose tolerance is reduced by at least 5% and more preferably any percentage in the range of 5 to 50%.

In an embodiment, an improvement in glucose regulation comprises one or more of the following characteristics: a HbA1C of less than or equal to 6.5%; less than 100 mg/dl fasting glucose; and/or less than 140 mg/dl oral glucose tolerance.

Location of Signal Application

Modulation of neural activity can be achieved by upregulating and/or down regulating neural activity of one or more target nerves or organs.

In some embodiments, electrodes can be positioned at a number of different sites and locations on or near a target nerve. Target nerves include the celiac nerve, the hepatic nerve, the vagal nerve, the splanchnic nerve, or some combination of these, respectively, of a patient. The electrode may also be positioned to apply a signal to an organ in proximity to the vagus nerve such as the liver, duodenum, jejunum, ileum, spleen, pancreas, esophagus, or stomach. In some embodiments, the electrode is positioned to apply an electrical signal to the nerve at a location near or distal to the diaphragm of the subject.

Electrodes may be positioned on different nerves to apply a down-regulating signal as opposed to an upregulating signal. For example, a down regulating signal can be applied on the vagus nerve and an upregulating signal applied to the splanchnic nerve. In some embodiments, the signals may be applied to reduce the neurally mediated reflex secretion by blocking the vagal nerves to the pancreas, and concurrently or subsequently, stimulate the splanchnic nerves to inhibit insulin secretion and/or upregulate the celiac nerve to stimulate GLP1 production.

In some embodiments, the electrode is positioned to apply a signal to a branch or trunk of the vagus nerve. In other embodiments, the electrode is positioned to apply a signal to an anterior trunk, posterior trunk or both. In some embodiments, the electrodes may be positioned at two different locations at or near the same nerve or on the nerve and on an alimentary tract organ. In some embodiments, the electrode is positioned below vagal enervation of the heart such as at a subdiaphragmatic location.

For example, FIG. 2 illustrates placement of a blocking electrode. Referring to FIG. 2, the baseline vagal activity is illustrated by the solid line of the proximal vagus nerve segment VNP. The remainder of the vagus and enteric nervous system are shown in reduced thickness to illustrate downregulation of tone. The pancreo-biliary output (and resulting feedback) is also reduced. In FIG. 2, the blocking electrode BE is shown high on the vagus relative to the GI tract innervation (e.g., just below the diaphragm), the sole blocking electrode could be placed lower (e.g., just proximal to pancreo/biliary innervation VN5). Blocking of the entire vagus as described above can be used to down-regulate the vagus for various benefits including treating a condition associated with impaired glycemic control. In some embodiments, the electrode may be placed on the celiac branch of the vagal nerve and provide for an upregulating signal.

In other embodiments, alternative designs for placing electrodes on or near the vagus nerve in a region of the esophagus E either above or below the diaphragm are provided.

Two paired electrodes may connect to a pulse generator for bi-polar signal. In other embodiments, a portion of the vagus nerve VN is dissected away from the esophagus E. An electrode is placed between the nerve VN and the esophagus E. The electrode is placed overlying the vagus nerve VN on a side of the nerve opposite electrode and with electrodes axially aligned (i.e., directly across from one another). Not shown for ease of illustration, the electrodes may be carried on a common carrier (e.g., a PTFE or silicone cuff) surrounding the nerve VN. Other possible placements of electrodes are described herein US 2005/0131485 published Jun. 16, 2005, which patent publication is hereby incorporated by reference.

Signal Frequency and Timing

In some embodiments, a downregulating signal has a frequency of at least 200 Hz and up to 5000 Hz. In other embodiments, the signal is applied at a frequency of about 500 to 5000 Hz. Applicant has determined a most preferred blocking signal has a frequency of 3,000 Hz to 5,000 Hz or greater applied by two or more bi-polar electrodes. Such a signal has a preferred pulse width of 100 micro-seconds (associated with a frequency of 5,000 Hz). It is believed this frequency and pulse width best avoid neural recovery from blocking and avoid repolarization of the nerve by avoiding periods of no signal in the pulse cycle. A short "off" time in the pulse cycle (e.g., between cycles or within a cycle) could be acceptable as long as it is short enough to avoid nerve repolarization. The waveform may be a square or sinusoidal waveform or other shape. The higher frequencies of 5,000 Hz or more have been found, in porcine studies, to result in more consistent neural conduction block. Preferably the signal is bi-polar, bi-phasic delivered to two or more electrodes on a nerve.

In some embodiments, a signal amplitude of 0.5 to 8 mA is adequate for blocking. Other amplitudes may suffice. Other signal attributes can be varied to reduce the likelihood of accommodation by the nerve or an organ. These include altering the power, waveform or pulse width.

Upregulating signals typically comprise signals of a frequency of less than 200 Hz, more preferably 10 to 150 Hz, and more preferably 10 to 50 Hz.

Selection of a signal that upregulates and/or downregulates neural activity and/or allows for recovery of neural activity can involve selecting signal type and timing of the application of the signal. For example, with an electrode conduction block, the block parameters (signal type and timing) can be altered by the pulse generator and can be coordinated with the stimulating signals. The precise signal to achieve blocking may vary from patient to patient and nerve site. The precise parameters can be individually tuned to achieve neural transmission blocking at the blocking site.

In some embodiments, the signal has a duty cycle including an ON time during which the signal is applied to the nerve followed by an OFF time during which the signal is not applied to the nerve. For example, the on time and off times may be adjusted to allow for partial recovery of the nerve, especially in situations where enteric accommodation may occur. In some cases, the downregulating and upregulating signals can be coordinated so that the upregulating signals are applied when down regulating signals are not being applied such as when the upregulating signals are applied at specific times or due to sensed events. In some embodiments, a sensed event indicates that an upregulating signal is applied and a down regulating signal is not applied for a time period relating to the sensed event, e.g. glucose exceeding a certain threshold or food entering the duodenum.

In some embodiments, subjects receive an implantable component 104. (FIG. 3) The electrodes 212, 212a are placed on the anterior vagus nerve AVN and posterior vagus nerve PVN just below the patient's diaphragm. The external antenna (coil 102) is placed on the patient's skin overlying the implanted receiving coil 105. The external control unit 101 can be programmed for various signal parameters including options for frequency selection, pulse amplitude and duty cycle. For blocking signals, the frequency options include 2500 Hz and 5000 Hz (both well above a threshold blocking frequency of 200 Hz). The vast majority of treatments are at 5,000 Hz, alternating current signal, with a pulse width of 100 microseconds. The amplitude options are 1-8 mA. For stimulating signals, a frequency is selected of less than 200 Hz.

Duty cycle could also be controlled. A representative duty cycle is 5 minutes of on time followed by 5 minutes of no signal. The duty cycle is repeated throughout use of the device.

Figure 12:
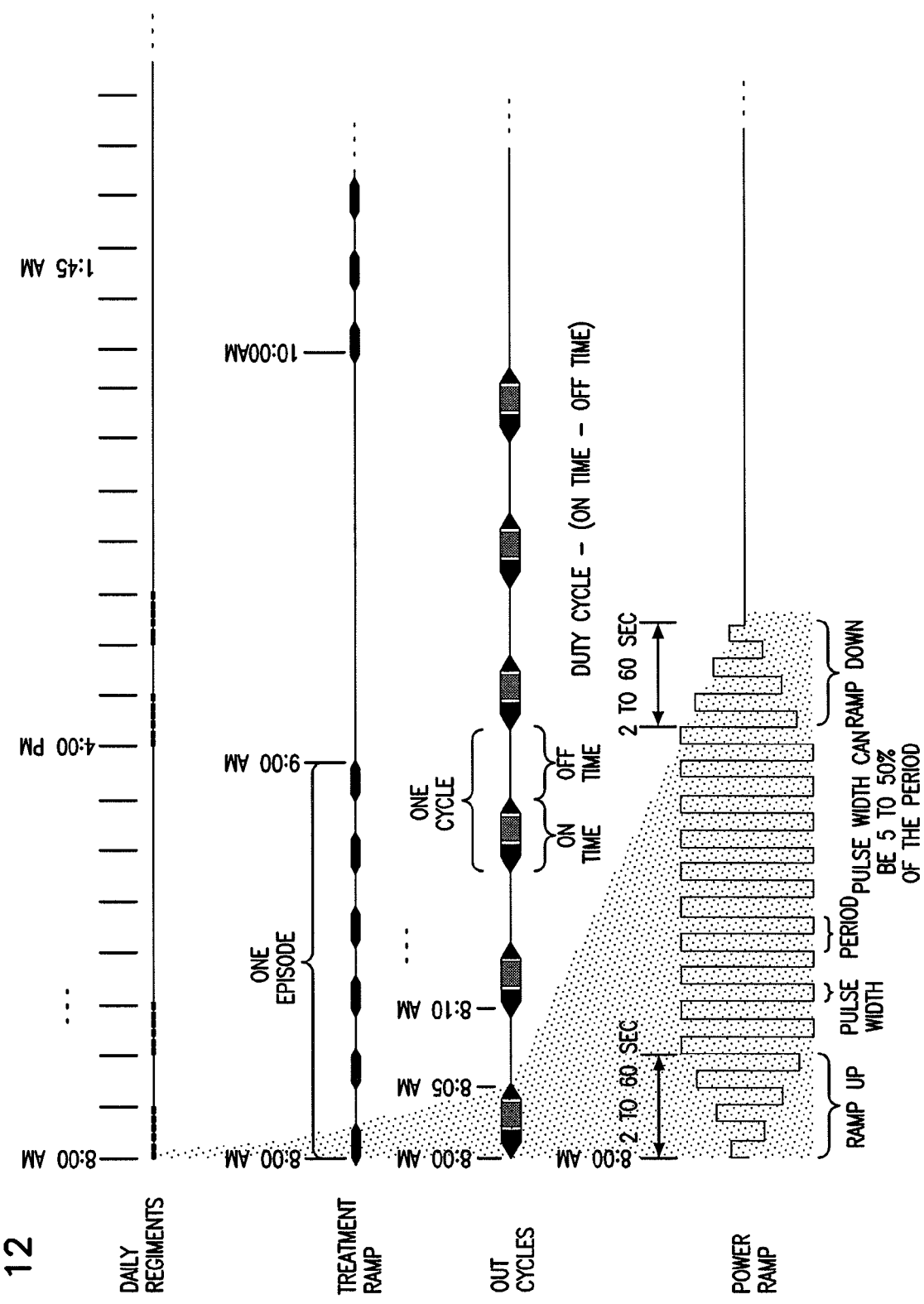
FIG. 12 shows a typical duty cycle.

FIG. 12 shows an exemplary duty cycle. Each ON time includes a ramp-up where the 5,000 Hz signal is ramped up from zero amperes to a target of 6-8 mA. Each ON time further includes a ramp-down from full current to zero current at the end of the ON time. For about 50% of the patients, the ramp durations were 20 seconds and for the remainder the ramp durations were 5 seconds. In some embodiments, the on time is elected to have a duration of no less than 30 seconds or no more than 180 seconds or both.

The use of ramp-ups and ramp-downs are conservative measures to avoid possibility of patient sensation to abrupt application or termination of a full-current 5,000 Hz signal. An example of a ramp-up for a high frequency signal is shown in U.S. Pat. No. 6,928,320 to King issued Aug. 9, 2005.

In some embodiments, a mini duty cycle can be applied. In an embodiment, a mini duty cycle comprises 180 millisecond periods of mini-ON times of 5,000 Hz at a current which progressively increases from mini-ON time to mini-ON time until full current is achieved (or progressively decreases in the case of a ramp-down). Between each of such mini-ON times, there is a mini-OFF time which can vary but which is commonly about 20 milliseconds in duration during which no signal is applied. Therefore, in each 20-second ramp-up or ramp-down, there are approximately one hundred mini-duty cycles, having a duration of 200 milliseconds each and each comprising approximately 180 milliseconds of ON time and approximately 20 milliseconds of OFF time.

In some embodiments, an upregulating signal may be applied in combination with a down regulating signal in order to improve glucose regulation, decrease the amount of calories ingested as well as increase the amount of GIP and/or GLP1. For example, a downregulating signal may be applied before and during meal, followed by an upregulating signal about 30 to 90 minutes after eating.

Normally a patient would only use the device while awake. The hours of therapy delivery can be programmed into the device by the clinician (e.g., automatically turns on at 7:00 AM and automatically turns off at 9:00 PM). In some cases, the hours of therapy would be modified to correspond to times when blood sugar fluctuates such as before a meal and 30-90 minutes after eating. For example, the hours of therapy may be adjusted to start at 5:00 AM before breakfast and end at 9:00 PM or later depending on when the last meal or snack is consumed. In the RF-powered version of the pulse generator, use of the device is subject to patient control. For example, a patient may elect to not wear the external antenna. The device keeps track of usage by noting times when the receiving antenna is coupled to the external antenna through radio-frequency (RF) coupling through the patient's skin.

Figure 8:
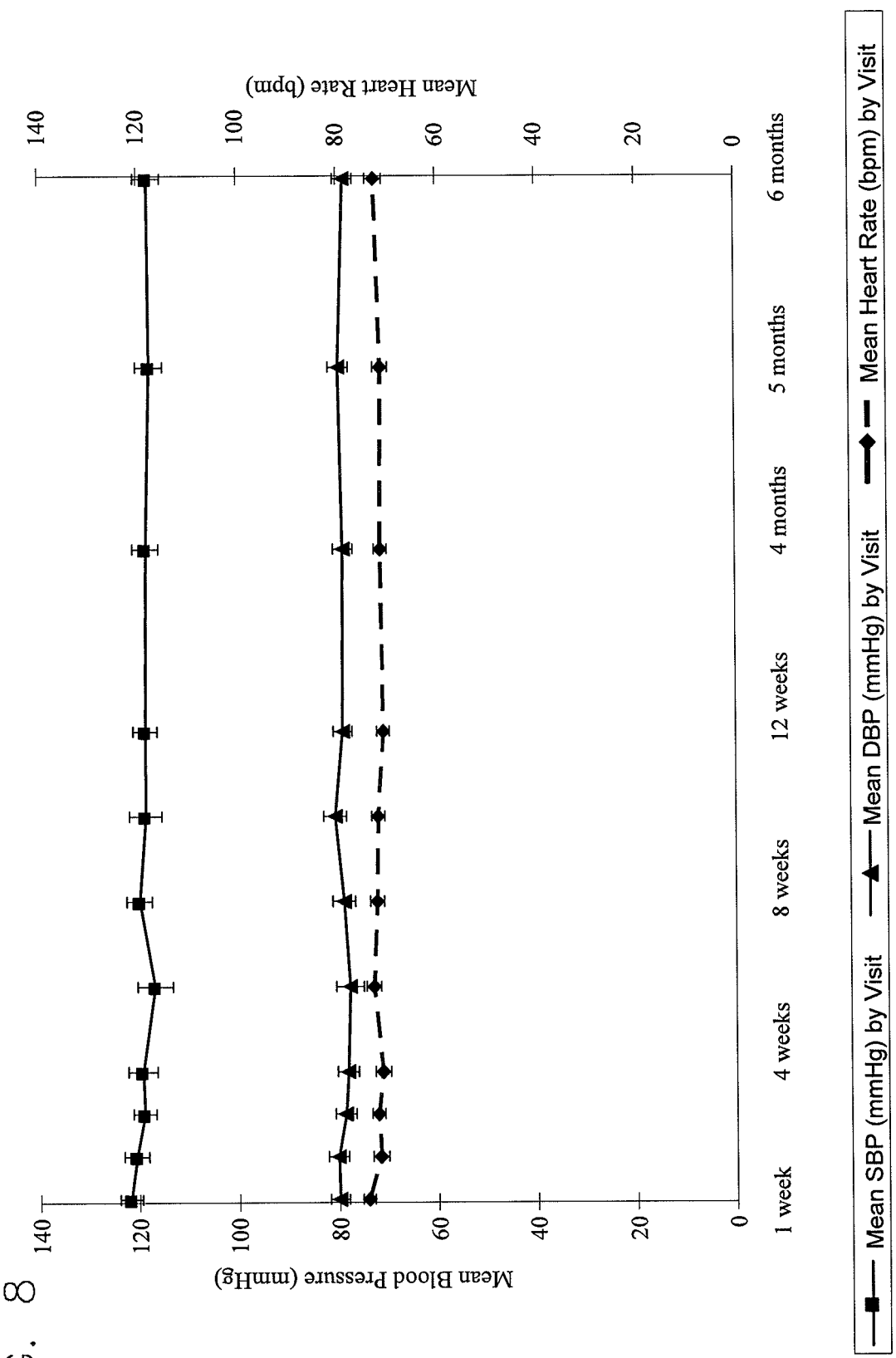
FIG. 8 shows effects of VBLOC on heart rate and blood pressure (mean±SEM)

In some cases, loss of signal contact between the external controller 101 and implanted pulse generator 104 occurs in large part to misalignment between coils 102, 105. (See FIG. 8). It is believed coil misalignment results from, at least in part, changes in body surface geometry throughout the day (e.g., changes due to sitting, standing or lying down). These changes can alter the distance between coils 102, 105, the lateral alignment of the coils 102, 105 and the parallel alignment of the coils 102, 105. Misalignment can be detected by the device and alignment of the coils adjusted to ensure that the signals are restored. The device may include a notification to the patient or physician if there has been a misalignment.

In some embodiments, the external component 101 can interrogate the pulse generator component 104 for a variety of information. In some embodiments, therapy times of 30 seconds to 180 seconds per duty cycle are preferred to therapy times of less than 30 seconds per duty cycle or greater than 180 seconds per duty cycle.

During a 10 minute duty cycle (i.e., intended 5 minutes of therapy followed by a 5 minute OFF time), a patient can have multiple treatment initiations. For example, if, within any given 5-minute intended ON time, a patient experienced a 35-second ON time and 1.5 minute actual ON time (with the remainder of the 5-minute intended ON time being a period of no therapy due to signal interruption), the patient could have two actual treatment initiations even though only one was intended. The number of treatment initiations varies inversely with length of ON times experienced by a patient.

The flexibility to vary average neural activity, such as vagal activity, gives an attending physician great latitude in treating a patient. For example, in treating diabetes or prediabetes, the blocking signal can be applied with a short "no blocking" time. If the patient experiences discomfort due to dysmotility, the duration of the "no blocking" period can be increased to improve patient comfort. Also, the reduction of enzyme production can result in decreased fat absorption with consequential increase of fat in feces. The blocking and no blocking duration can be adjusted to achieve tolerable stool (e.g., avoiding excessive fatty diarrhea). The control afforded by the present invention can be used to prevent the enteric nervous system's assumption of control since vagal activity is not completely interrupted as in the case of a surgical and permanent vagotomy.

While patient comfort may be adequate as feedback for determining the proper parameters for duration of blocking and no blocking, more objective tests can be developed. For example, the duration of blocking and no blocking as well as combination with upregulating signals can be adjusted to achieve desired levels of glucose regulation. Such testing can be measured and applied on a per patient basis or performed on a statistical sampling of patients and applied to the general population of patients.

In some embodiments, a sensor may be employed. A sensing electrode SE can be added to monitor neural activity as a way to determine how to modulate the neural activity and the duty cycle. While sensing electrode can be an additional electrode to blocking electrode, it will be appreciated a single electrode could perform both functions. The sensing and blocking electrodes can be connected to a controller as shown in FIG. 3. Such a controller is the same as controller 102 previously described with the additive function of receiving a signal from sensing electrode.

In some embodiments, the sensor can be a sensing electrode, a glucose sensor, or sensor that senses other biological molecules or hormones of interest. When the sensing electrode SE yields a signal representing a targeted maximum vagal activity or tone (e.g., 50% of baseline as shown in FIG. 6) the controller with the additive function of receiving a signal from sensing electrode energizes the blocking electrode BE with a blocking signal. As described with reference to controller 102, controller with the additive function of receiving a signal from sensing electrode can be remotely programmed as to parameters of blocking duration and no blocking duration as well as targets for initiating a blocking signal or upregulating signal.

In some embodiments, of the apparatus and method described herein use recovery of the vagus nerve to control a degree of down-regulation of vagal activity. This gives a physician enhanced abilities to control a patient's therapy for maximum therapeutic effectiveness with minimum patient discomfort. Vagal neural blocking simulates a vagotomy but, unlike a vagotomy, is reversible and controllable.

Agents that Alter Impairment of Glycemic Control of the Subject

The disclosure provides methods for treating a condition associated with impaired glucose regulation that include neuroregulation as well as administering to a subject a composition comprising an agent that affects glucose control in a subject. In some embodiments, the agent increases the amount of insulin present in the blood. In other embodiments, the agent increases insulin sensitivity. In some embodiments, the agent reduces endogenous glucose production and/or glucose absorption.

Several pathways are known to affect energy balance. Pathways include gut-hypothalamic axis (e.g. ghrelin), gut-hindbrain axis (e.g. vagus nerve), peripheral tissue (adipose tissue, skeletal muscle)-hypothalamic axis (e.g. leptin), and hypothalamic-hindbrain axis (neural projections). In particular, the hypothalamus (forebrain) and the area postrema (hindbrain) are 2 regions of the central nervous system which are thought to play orchestrating roles in the human energy homeostasis. It has been documented that there are neural connections between these two regions enabling communications and complementary, as well as, redundant effects on body energy balance. Numerous hormones, enzymes, neurotransmitters, and other mediators are released from different parts of these pathways and can have influences on these regions of the central nervous system. Utilization of distinct treatment modalities that involve different parts of these pathways and brain regions, thus altering the communication between the central nervous system and gut, pancreas, liver, muscle, and fat cells may be of importance in combinatorial therapy that is highly effective, robust, and durable.

Agents that affect impaired glucose control can be selected based on an ability to complement treatment of applying a signal to alter neural activity of a target nerve. As described herein, an agent is selected that may provide a complementary or synergistic effect with the application of signal to modulate neural activity on a target nerve such as the vagus nerve. A synergistic or complementary effect can be determined by determining whether the patient has an improvement in glycemic control as described herein as compared to one or both treatments alone.

In some embodiments, agents that act at a different site (e.g. hypothalamus or pituitary) or through a different pathway may be selected for use in the methods described herein. Agents that complement treatment are those that include a different mechanism of action for affecting the glycemic control of the subject. In some embodiments, a synergistic effect may be observed with an agent that does not affect glucose digestion and/or delay gastric emptying, such as an agent that increases insulin secretion, insulin sensitivity, and/or decreases endogenous glucose production. Such agents include insulin, amylin analogues, insulin secretagogues, sulfonylureas, meglitinides and PPAR alpha, gamma and delta agonists.

An agent may also or in addition be selected to be administered that may have undesirable side effects at the recommended dosage that prevents use of the agent, or that provides inadequate glycemic control. In addition, patients that have hypertension, cardiac conditions, liver disease, or renal disease may not be able to tolerate treatment with one or more of the agents at the recommended dosage due to adverse side effects.

Agents that have undesirable side effects include Avandia (rosiglitazone; PPAR-gamma agonist) which has been shown to have adverse effects on cardiovascular conditions and cause weight gain. Drugs that inhibit or slow gastric emptying, such as amylin analogs or GLP-1 analogs, or drugs that are irritants to the GI track, such as metformin (biguinide) can cause nausea, vomiting, and diarrhea. Drugs that alter breakdown and absorption of carbohydrate in the GI track, such as Precose (acarbose; alpha-glucosidase inhibitor) can cause diarrhea and flatulence. Drugs that increase blood insulin concentrations, such as exogenous insulin administration, sulfonylureas, and meglitinides can cause hypoglycemia and weight gain.

Combining administration of a drug with undesirable side effects with modulating neural activity on a target nerve may allow for administration of the drugs at a lower dose thereby minimizing the side effects. In addition, a drug may be selected that has altered pharmacokinetics when absorption is slowed by a delay in gastric emptying due to neural down-regulation as described herein. In other embodiments, the recommended dosage may be lowered to an amount that has fewer adverse side effects. In embodiments, it is expected that the recommended dosage may be able to be lowered at least 25%. In other embodiments, the dosage can be lowered to any percentage of at least 25% or greater of the recommended dose. In some embodiments, the dosage is lowered at least 25, 30, 35, 40, 45, 50, 55, 60, 65, 70, 75, 80, 85, 90, 95, or 100% of the recommended dosage.

In an embodiment, a method provides a treatment for a condition associated with impaired glycemic control. A method comprises selecting a drug useful for treating Type 2 diabetes or impaired glucose regulation and having a recommended dosage for efficacy where a patient is likely to experience disagreeable side effects at said recommended dosage; and treating the patient with a concurrent treatment comprising: applying an intermittent neural block to a target nerve of the patient at multiple times per day and over multiple days with the block selected to down-regulate afferent and/or efferent neural activity on the nerve and with neural activity restoring upon discontinuance of said block; and administering said drug to the patient at a dosage less than said recommended dosage. In some embodiments, the effective dosages for treating a condition associated with impaired glycemic control for such a patient are associated with disagreeable side effects contributing to said patient not complying with a drug treatment. In some embodiments, patients are those that have an eating disorder, hypertension, cardiac conditions, liver, or renal disorder and may not be able to tolerate treatment with one or more of the agents.

Agents that increase the amount of insulin present or the amount of insulin secreted are agents that can improve glycemic control of the patient. Such agents include sulfonylureas, meglitinides, Dipeptidyl peptidase IV (DPP4) inhibitors, insulin, insulin analogs, and GLP-1 analogs.

Agents that increase the sensitivity of cells to insulin are agents that can improve glycemic control of the patient. Such agents include biguinides such as metformin and PPAR gamma agonists such as rosiglitazone and piglitazone.

Agents that inhibit the production of glucose or the digestion of carbohydrates are agents that can improve glycemic control of the patient. Such agents include biguanides, alpha glycosidase inhibitor, amylin analogs, DPP4 inhibitors, and GLP-1 analogs.

Agents that decrease the effects of gherlin may also be useful in diabetes therapies including protein kinase A inhibitors, neuropeptide Y receptor inhibitors, and growth hormone secretatogue receptors.

Agents that enhance the amount of GIP or GLP-1 or that decrease the amount ghrelin can be advantageously combined with neural modulation therapy. For example, up or downregulation of the nerve can be applied to increase the amount of GIP and/or GLP-1 in combination with an agents such as a DPP4 inhibitor which inhibits the breakdown of GLP-1. In an embodiment, the vagus nerve can be downregulated by applying an intermittent reversible downregulating signal to the vagus nerve in combination with a DDP4 inhibitor such as vildagliptin or sitagliptin.

One or more of these agents may be combined for treatment especially when single drug treatment alone does not provide adequate glycemic control. Any of the FDA approved drugs for treating diabetes may also be combined with the methods as described herein.

Dosages for administration to a subject can readily be determined by one of skill in the art. Guidance on the dosages can be found, for example, by reference to other drugs in a similar class of drugs. For example, dosages have been established for any of the approved drugs or drugs in clinical trials and the range of dose will depend on the type of drug. For example, pramlintide dosages range from about 240 micrograms up to 720 micrograms per day. Dosages associated with adverse side effects are known or can also be readily determined based on model studies. A determination of the effective doses to achieve improved glycemic control while minimizing side effects can be determined by animal or human studies.

Agents will be formulated, dosed, and administered in a fashion consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners. The agent need not be, but is optionally formulated with one or more agents currently used to prevent or treat the disorder in question. The effective amount of such other agents depends on the amount of agent that improves glycemic control of the subject present in the formulation, the type of disorder or treatment, and other factors discussed above. These are generally used in the same dosages and with administration routes as used hereinbefore or about from 1 to 99% of the heretofore employed dosages.

Therapeutic formulations comprising the agent are prepared for storage by mixing the agent having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated. In such embodiments, the compounds have complementary activities that do not adversely affect each other. Such molecules are suitably present in combination in amounts that are effective for the purpose intended.

The therapeutic agent is/are administered by any suitable means, including parenteral, subcutaneous, orally, intradermal, intraperitoneal, and by aerosol. Parenteral infusions include intramuscular, intravenous, intraarterial, intraperitoneal, or subcutaneous administration. Pumps may be utilized as well as drug eluting devices and capsules.

Example 1

Material and Methods/Experimental Design

An open-label, prospective, baseline-controlled, three-center clinical study was conducted to evaluate feasibility and safety and efficacy of a device as described herein that causes intermittent electrical blocking of the anterior and posterior vagal trunks. The participating centers include Flinders Medical Centre, Adelaide, Australia; Instituto National de la Nutricion (INNSZ), Mexico City, Mexico; and, St. Olavs University Hospital, Trondheim, Norway.

Patients

Male or female obese subjects (BMI 31.5-55 kg/m$^2$) 25-60 years of age inclusive, were recruited at the three centers. The study assessed device safety and efficacy for 6 months.

Ability to complete all study visits and procedures was an eligibility requirement. Relevant exclusion criteria included: current type 1 diabetes mellitus (DM) or type 2 DM poorly controlled with oral hypoglycemic agents or with associated autonomic neuropathy, including gastroparesis; treatment with weight-loss drug therapy or smoking cessation within the prior three months or reductions of more than 10% of body weight in the previous 12 months; prior gastric resection or other major abdominal surgery, excluding cholecystectomy and hysterectomy; clinically significant hiatal hernias or intra-operatively determined hiatal hernia requiring surgical repair or extensive dissection at esophagogastric junction at time of surgery; and presence of a permanently implanted electrical powered medical device or implanted gastrointestinal device or prosthesis.

Concurrent treatment for thyroid disorders, epilepsy or depression with tricyclic agents was acceptable for participation if the treatment regimen was stable for the prior six months.

Implantation of Device

The device included two electrodes (one for each vagal trunk), a neuroregulator (pulse generator) placed subcutaneously and an external controller to program the device.

Under general anesthesia, two leads (electrodes) of the vagal blocking system (FIG. 4) were implanted laparoscopically. Device implantation by the experienced surgeons participating in the study typically took 60 to 90 minutes; five ports were usually used. The electrode itself had an active surface area of 10 mm$^2$ and was "c"-shaped to partially encircle the nerve.

Intra-abdominal dissection and electrode placement were accomplished in the following sequence. The gastrohepatic ligament was dissected to expose the esophagogastric junction (EGJ), and the stomach was retracted downward and laterally in order to keep slight tension on the EGJ. To locate the posterior vagal trunk, the right diaphragmatic crus was identified and separated from its esophageal attachments. The anterior vagal trunk was identified by locating it as it courses through the diaphragmatic hiatus. After both vagal trunks had been identified, a right angle grasper was used to dissect a 5 mm window underneath the posterior vagal trunk. The electrode was then placed by positioning a right angle grasper through the window that had been created under the vagal trunk. The electrode's distal suture tab was then grasped, and the electrode was pulled into place, seating the nerve within the electrode cup. The same steps were repeated to place a second electrode around the anterior vagal trunk. Finally, each electrode was secured in position using a single suture placed through each electrode's distal suture tab and affixed to the outer layers of the esophagus.

The leads were then connected to the neuroregulator, and it was implanted in a subcutaneous pocket in the mid-line just below the xiphoid process. Proper electrode placement was then determined in two different ways at implant. First, correct anatomic electrode-nerve alignment was verified visually. Secondly, effective electrical contact was verified using impedance measurements intra-operatively and at frequent intervals thereafter. After recovery from the surgery, a programmable external controller which contained a rechargeable power source was used to communicate transdermally with the implanted neuroregulator via an external transmit coil Electrical Signal Application The external controller was programmed for frequency, amplitude and duty cycle. The therapeutic frequency selected to block neural pulses on the vagal trunks was 5000 Hz, based on animal studies of vagal inhibition of pancreatic exocrine secretion. Amplitudes utilized ranged from 1-6 mA; however, in almost all instances, the amplitude was 6 mA. The device was activated in the morning, and turned off before sleep. The protocol specified an algorithm of five minutes of blocking alternating with five minutes without blocking for 12 hours per day. Effective electrical contact was verified using impedance measurements at frequent intervals postoperatively.

Experimental Therapy and Follow-Up Studies

In order to focus on the effects of the vagal blocking system, the study subjects were precluded from receiving either concomitant diet or behavioral counseling or drug therapy for obesity during the 6 month trial period. All study participants were implanted with the device. Two weeks post-implant, intermittent, high-frequency electrical algorithms were commenced in all subjects. Subjects were followed weekly for 4 weeks, then every two weeks until 12 weeks and then monthly visits for body weight, physical examination and adverse event (AE) inquiry. In addition, 12-lead electrocardiograms (ECGs) and clinical chemistries were analyzed at a core laboratory.

Calculation of Percentage Excess Weight Loss

Ideal body weight was calculated by measuring each subject's height and then determining the body weight that would result in a BMI of 25.0 for that subject, i.e., ideal body weight (kg)=25×height$^2$ (m). EWL was calculated by dividing weight loss by excess body weight [(total body weight)−(ideal body weight)] and multiplying by 100. Thus, EWL %=(weight loss (kg)/excess body weight (kg))×100.

Calorie Intake, Dietary Composition, Satiation, Satiety and Vagal Function Studies Two sub-studies were performed to assess the effect of the treatment on satiation, calorie intake and vagal function and their relationship to the degree of weight loss.

In one sub-study (Sub-study A), which was conducted at a single center (Flinders Medical Centre, Adelaide, Australia), all subjects were followed with seven-day diet records to quantify changes in calorie intake, dietary composition, satiation at meals and satiety (reduced hunger) between meals. These assessments were conducted pre-implant and after four weeks, 12 weeks and 6 months of vagal blocking via a diet diary completed by each subject. At each visit, each seven-day diet record, including quantification of carbohydrates, fat and protein as a percent of total caloric intake, was verified during a detailed interview with a nutritionist. A validated program (FoodWorks™) for determining nutrient and calorie content in food was used. In addition, at each visit, questionnaires with standard, horizontal (100-mm) visual analog scales (VAS) were used to assess satiation and satiety using both one-week and 24-hour recall.

In a second sub-study (Sub-study B) conducted after 12 weeks of vagal blocking at two centers (Flinders Medical Centre, Adelaide Australia and Instituto National de la Nutricion, Mexico City, Mexico), a standardized sham feeding protocol was used in order to assess vagal down-regulation. The endpoint of down-regulation was measured as the inhibition of plasma pancreatic polypeptide (plasma PP) response following sham feeding. Subjects were instructed to fast for at least eight hours prior to the test. Two baseline plasma samples were obtained for PP levels at −5 and −1 minutes, followed by a 20-minute sham feeding using the "chew and spit" method with blood samples collected every 5 minutes. Subjects were instructed to avoid swallowing food or saliva to eliminate nutrient activation of pancreatic secretion. Plasma was stored at −70 degrees Celsius, and transferred on dry ice for PP levels to be measured by standard radio-immunoassay (Mayo Medical Laboratories, Rochester, Minn., USA). A subset of these subjects (n=10) also had sham feeding and plasma PP levels prior to implantation as part of the familiarization of the centers with the performance of the test procedure, prior to conducting the test as planned 12 weeks post-therapy.

Data and Statistical Analysis

Baseline characteristics and demographics were summarized using descriptive statistics. Continuous variables were summarized by mean values and corresponding standard errors of the mean (SEM). Categorical (including binary) variables were summarized by frequency distributions.

The primary endpoint for assessing the effect on weight loss was the mean percent excess weight loss (EWL %) at specified time points (4 and 12 weeks and 6 months) and compared to zero in a two-sided, one-sample t-test at the 5% significance level. P-values reported were unadjusted for multiple comparisons. However, the statistical significance was not altered after applying Hochberg's multiple comparison procedure. Additionally, a mixed model, repeated measures regression analysis was conducted evaluating effects of treatment on EWL % over time.

Changes in heart rate and blood pressure were summarized over time, using mean and SEM. ECG recordings were collected and analyzed by an independent core lab (Mayo Medical Laboratories, Rochester, Minn., USA). Clinical chemistries (amylase, lipase, and blood glucose) were collected and analyzed according to mean changes from baseline as well as categorically to determine the frequency of abnormal findings during follow-up.

Adverse events (AE) were tabulated and reported. No formal statistical analyses of adverse events were performed on the rate of occurrence of adverse events as no a priori hypotheses were specified.

The changes from baseline in the percentage composition of each dietary macronutrient component (carbohydrate, protein and fat) was compared to zero in a two-sided, one-sample t-test at each follow-up visit (4 and 12 weeks and 6 months) and also in a mixed model, repeated measures regression model.

Visual analog scale (VAS) questionnaires were completed by each subject at every follow-up visit to assess satiation and satiety (reduced hunger). Mean changes (±SEM) in responses from baseline were calculated at each visit.

Plasma PP levels in response to sham feeding were computed as means (±SEM) at 5, 10, 15 and 20 minutes into the sham feeding in participants who underwent the studies pre-implant and after 12 weeks of vagal blocking. The proportion of subjects with plasma PP increases less or more than 25 pg/ml (the cut-off value for abnormal vagal function in the literature) was calculated and the average weight loss for the two groups compared using a two-tailed, unpaired t-test.

Results

Participants, Demographics and Outcomes of Surgical Procedure

Thirty-one subjects (mean body mass index 41.2±0.7 kg/m$^2$; range 33-48) received the device. Demographics, including type 2 diabetes mellitus subjects, are shown in Table I.

TABLE I

Demographics of study population (mean ± SEM)

| Demographics | All subjects |
|---|---|
| Number | 31 |
| Age (yrs) | 41.4 ± 1.4 |
| Gender | 26 female/5 male |
| Race/ethnicity | 12 hispanic/19 white-not hispanic |
| Baseline BMI, kg/m$^2$ | 41.2 ± 0.7 |
| Pts with type 2 diabetes mellitus | 3 |

There have been no major intra-operative complications with implantation of the device. Specifically, we have not encountered organ perforation, significant bleeding, post-operative intra-peritoneal infections, or electrode migration or tissue erosion. The devices were left in place after the 6 month study. Those participants continue to be followed as part of a safety cohort for such a device, and further studies are being conducted to determine whether the electrical parameters can be modified to maximize the efficacy of the device.

Weight Loss

Figure 7:
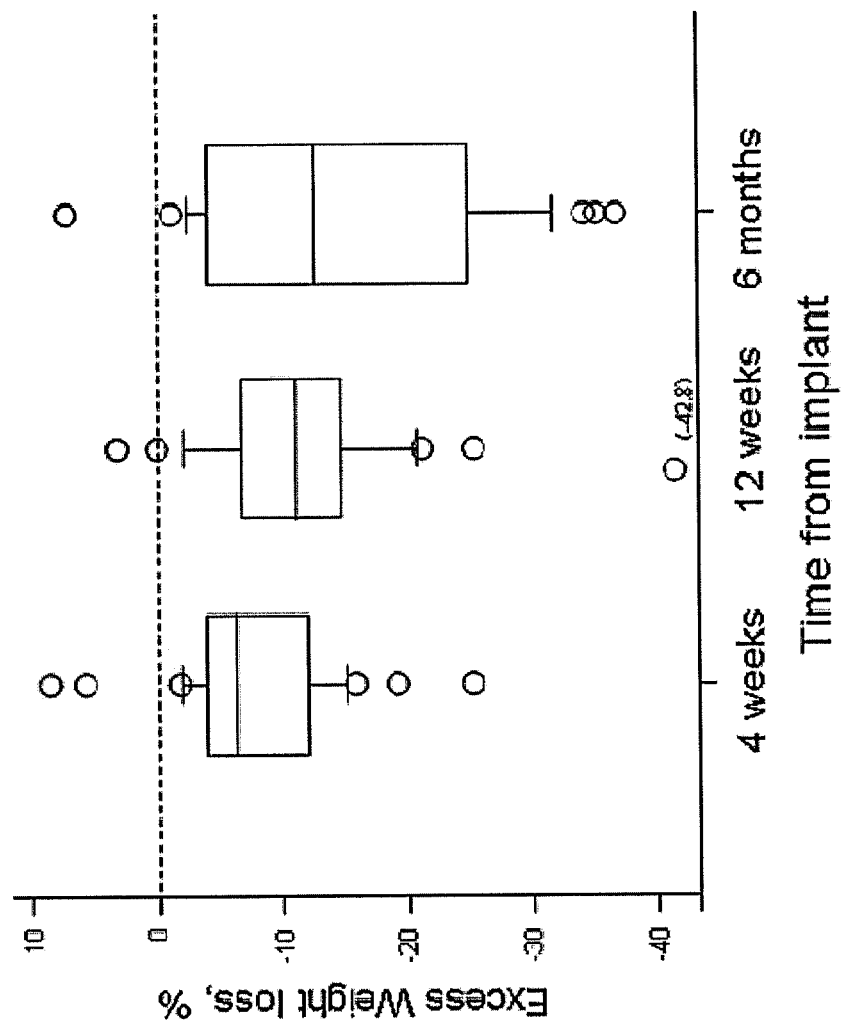
FIG. 7 shows effect of vagal blocking therapy (VBLOC) on percentage excess weight loss (% EWL) from time of device implant. Data shown are Excess Weight Loss (EWL) % changes (median, interquartile distribution, and $5^{th}$ and $95^{th}$ percentiles) with individuals' data plotted for those beyond those percentiles. Note that while a few individuals did not lose any weight, 10% patients had >30% EWL at six months, and 25% patients had >25% EWL.

Mean excess weight loss at 4 and 12 weeks and 6 months following device implant was 7.5%, 11.6% and 14.2%, respectively (all changes were significant compared to baseline, p<0.0001). Beneficial overall effects of treatment were observed at all three centers. FIG. 7 shows the distribution of EWL percentage changes, including the median, interquartile distribution and 5$^{th}$ and 95$^{th}$ percentile with individuals' data plotted for those beyond those percentiles. Note that while a few individuals did not lose any weight, three patients had >30% EWL at six months, and a quarter of the patients had >25% EWL.

Adverse Events

There were no deaths, no serious adverse events (SAE) related to either the medical device or VBLOC therapy and no unanticipated adverse device effects during the study. Three subjects, who had SAEs that were unrelated to the device or with vagal blocking therapy, required brief hospitalization: one post-operative lower respiratory tract infection (1 day hospitalization), one subcutaneous implant site seroma (3 days hospitalization), and one case of *Clostridium difficile* diarrhea two weeks into the trial period (5 days hospitalization). These three SAEs were completely reversible, and the patients continued in the study.

There were no clinically significant changes in either clinical chemistries or ECG findings during the 6 month study as evaluated by an external data safety monitoring committee (data not shown). There were small decreases in heart rate and systolic and diastolic blood pressures (FIG. 8) that were deemed to be non-clinically significant.

Calorie Intake, Dietary Composition, Satiation and Satiety: Sub-Study A

Figure 9:
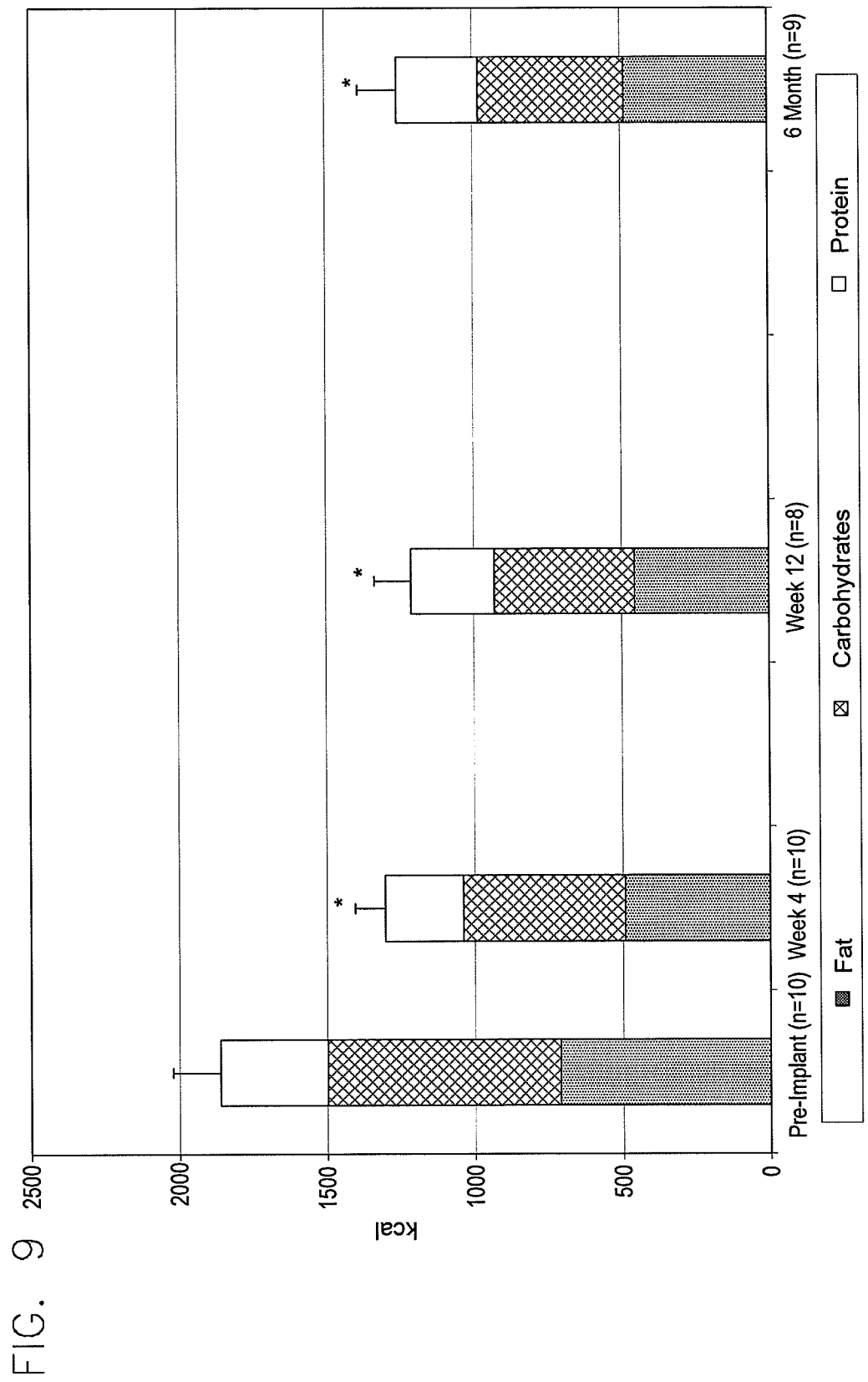
FIG. 9 shows vagal blocking effects on calorie intake and dietary composition. Each visit shows a significant reduction from baseline (all $p \leq 0.01$)
Figure 10A:
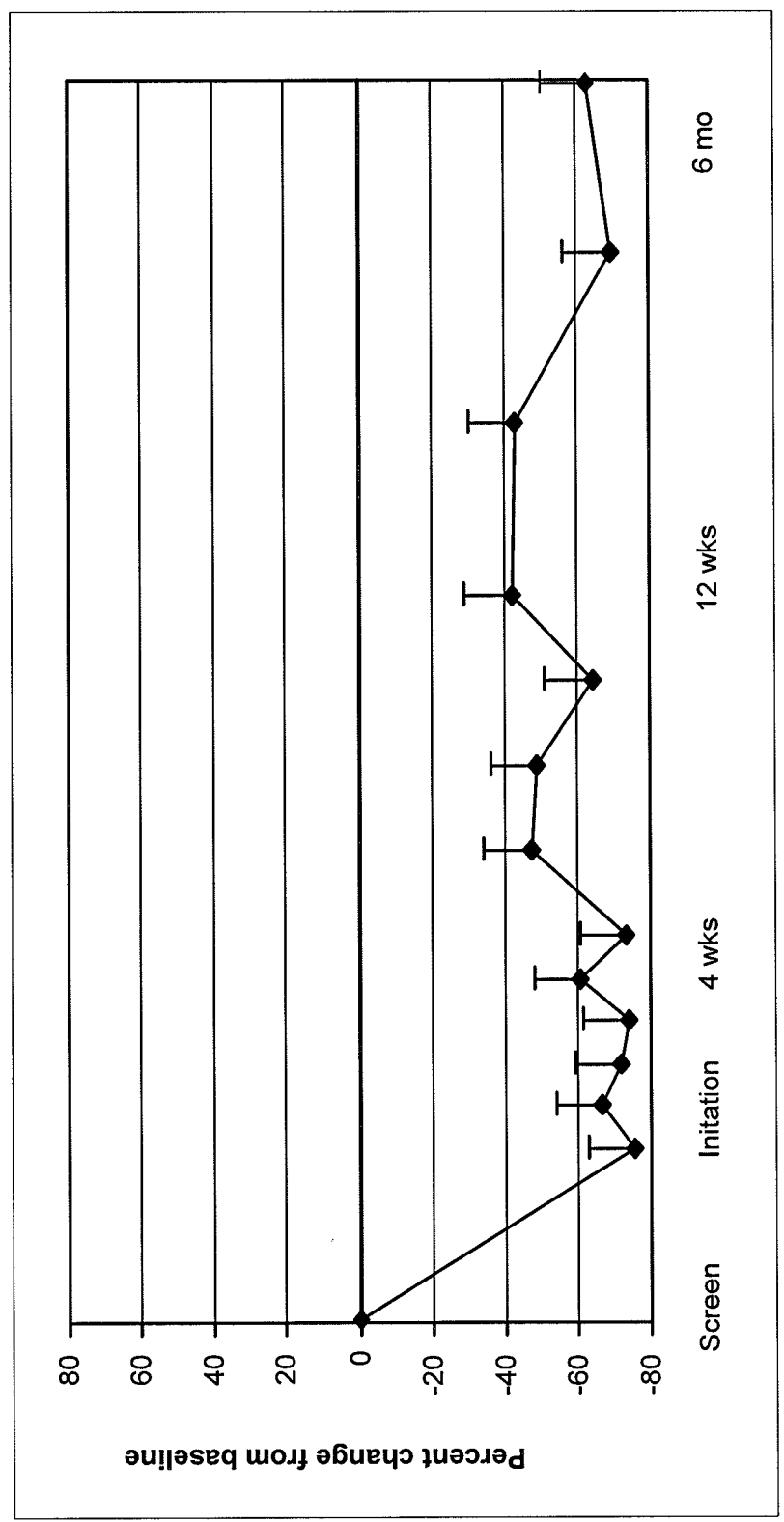
FIG. 10 shows effects of VBLOC on satiation and satiety utilizing visual analogue scales (VAS) expressed as percent change from baseline. Overall, the results show a significant reduction from baseline. A. Time to satiation (fullness) at meal based on 24 hour recall; B. Hunger between meals (satiety) based on 24 hour recall, Decreases represent reduced hunger.
Figure 10B:
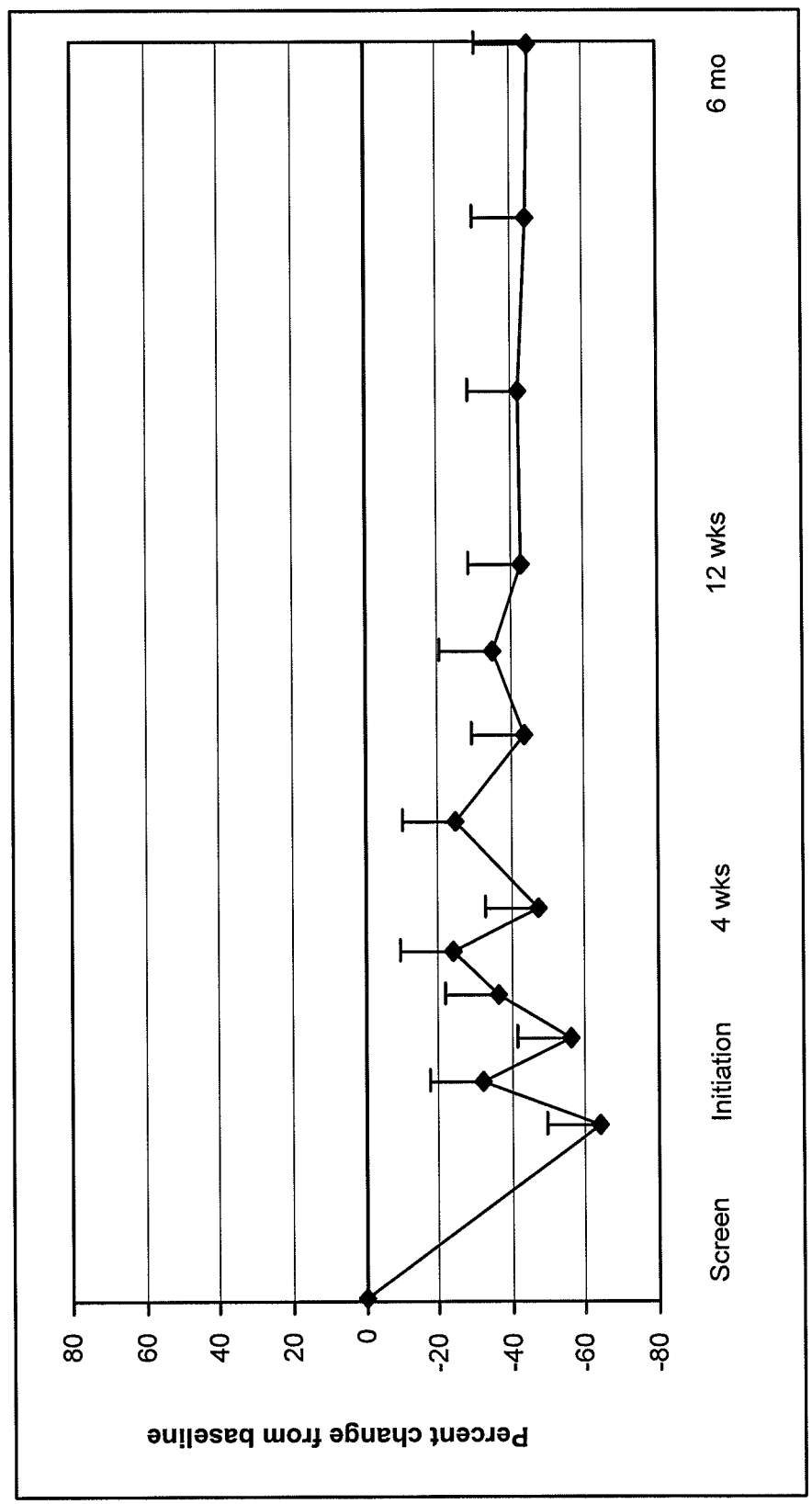

Changes in calorie intake, dietary composition, satiation and satiety (decreased hunger) were assessed in all ten subjects who completed the visits and procedures at Flinders Medical Centre, Adelaide, Australia as part of Sub-study A. Calorie intake decreased by >30% at 4 and 12 weeks and 6 months (p<0.01, all time points, FIG. 9). Relative amount of carbohydrate, protein, and fat intake stayed stable. In addition, VAS questionnaire data based on 24-hour recall demonstrated that subjects reported earlier satiation (fullness) at main meals (FIG. 10A, p.<0.001) and enhanced satiety (decreased hunger) between meals (FIG. 10B, p=0.005) in the 6 month time period.

Vagal Function: Sub-Study B

Figure 11:
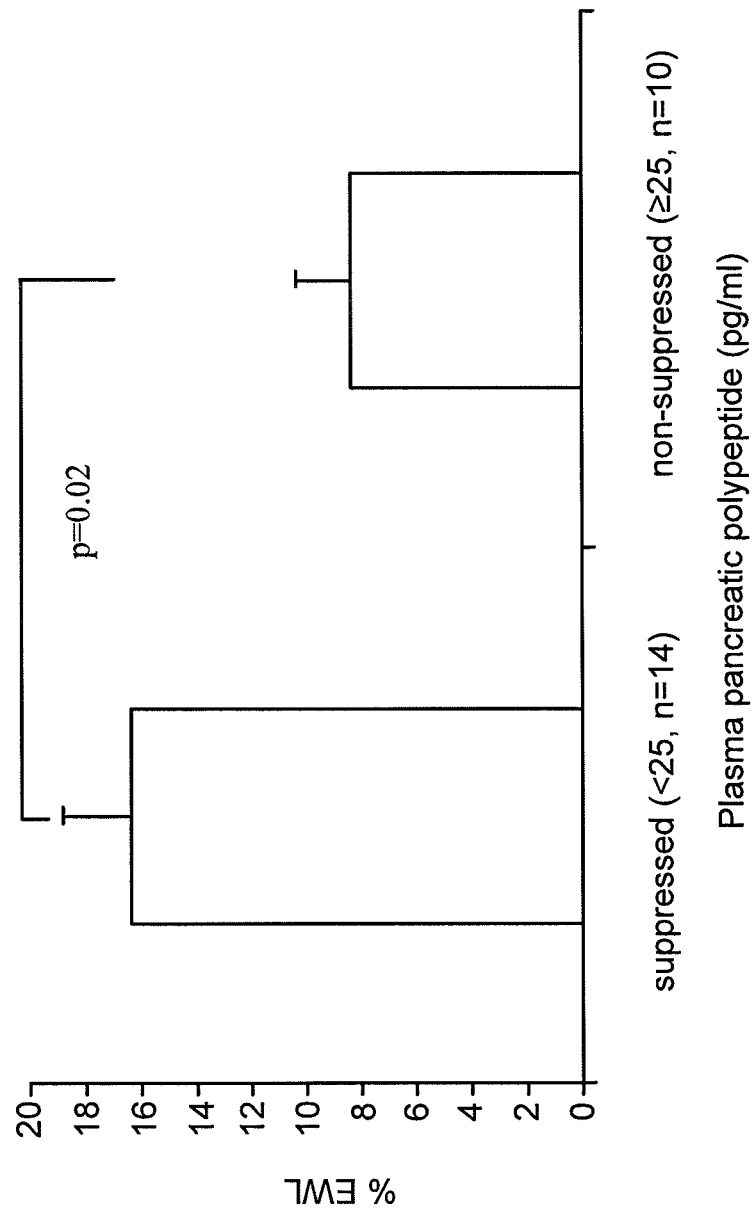
FIG. 11 shows effect of pancreatic polypeptide suppression on % EWL at 12 wks (mean±SEM, p=0.02).

Twenty-four study patients completed the sham feeding protocol after 12 weeks of intermittent vagal blocking as part of Sub-study B. Prior to implant, sham feeding resulted in normal plasma PP response (increases above baseline of ≧25 pg/ml: 42±19 pg/ml). Following 12 weeks of vagal blocking, PP responses at 20 min were suppressed, so that the increases in plasma PP were on average <25 pg/ml (20±7 pg/ml). The percentages of subjects with blunted PP response (<25 pg/ml) were 88, 79, 71 and 67% at 5, 10, 15 and 20 min, respectively. Importantly, a subset analysis of data at 12 weeks showed that weight loss was significantly greater in the 14 patients who never had plasma PP rise >25 pg/ml over fasting, compared to the 10 patients who had plasma PP rise >25 pg/ml (p=0.02, FIG. 11).

Change in Glycemic Control

A subset of patients from the above study, as well as other clinical trial studies, were monitored for hemoglobin A1c using standard methods. At baseline, the mean of 10 patients was 8.2% HbA1c. After 4 weeks the mean HbA1C dropped to 7.1%. Improvements were noted as early as 4 weeks and before substantial weight loss was observed.

TABLE 2

| Time point | HemoglobinA1c (mean ± SEM) |
|---|---|
| Baseline | 8.2 ± 0.6% |
| Week 4 | 7.1 ± 0.4% |
| Improvement | −1.1 ± 0.3%* |

N = 10
*p = 0.002

Discussion

In this clinical trial of an implantable system that delivers intermittent vagal blocking (VBLOC therapy), we report here on initial data on safety and efficacy—as measured by EWL %. In addition, the sub-studies conducted have shown that the weight loss is associated with decreased calorie intake, earlier satiation at meals and enhanced satiety (decreased hunger) between meals. A subset of patients demonstrated a significant decrease in HbA1c as early as 4 weeks. Vagal inhibition, measured by reduced plasma PP response during sham feeding (<25 pg/ml), was demonstrated at three months post implant, suggesting that the electrical signal delivered via VBLOC therapy is able to maintain vagal blockade and to induce the clinical effects on satiation and weight loss.

The magnitude of EWL ranged from 1.2 to 36.8% at six months, suggesting that there is variability in the response and room for maximizing the benefit from such a treatment approach. It should be noted that a single study subject, who was non-compliant during the entire course of the study, did gain weight. This subject's compliance was deemed inadequate as reflected by the fact that therapy delivery was less than 25% of that prescribed during the 6 month study period. Variable response to vagal block may reflect several possibilities including failure to apply the electrical treatment (compliance), inter-individual differences in the "capture" of vagal function (as illustrated by the suboptimal suppression of the plasma PP response to sham feeding), and technical factors in the device, such as variability in the position of the external coil relative to the internal neuroregulator.

Weight reduction observed in this study was progressive out to 6 months of follow-up without an apparent plateau. It is important to note that this effect on weight was achieved without the additional benefit of dietary or behavioral modification, which may augment weight reduction with any intervention. While we cannot completely exclude a placebo effect, given the open trial design, we expect that this is unlikely since the reduced caloric intake, time to satiation at meals and hunger between meals were achieved early after onset of treatment, were maintained throughout the 6 month study, and were associated with significant and sustained weight loss.

The present studies provide some insights on the mechanism for the weight loss associated with VBLOC therapy. The vagus nerve has pivotal roles in multiple aspects of alimentary tract function, including gastric accommodation, contractions and emptying and pancreatic exocrine secretion. It has also been reported that the vagus nerve plays an important role in release of gut-derived hormones known to have acute and profound effects on food intake and appetite. A prime example of such a vagally-controlled hormone is ghrelin, an orexigenic peptide largely produced in the foregut. Ghrelin concentrations increase with short-term food deprivation and/or weight loss and decrease rapidly with food intake. Thus, it is believed that ghrelin has an anticipatory role in food intake. Bilateral vagotomy in rats has been reported to completely eliminate the expected increase in ghrelin levels induced by food deprivation. This elimination of the ghrelin response may be a mechanism whereby vagal blocking results in reduced food intake and augmented satiation.

Safety of the novel device and electrical signal applied as described herein is supported by the fact that the only notable complications were three infections related to the surgical procedure or C. difficile diarrhea, all of which were considered by an independent data safety monitoring committee to be unrelated to the device itself. There were no major intra-operative complications. Specifically, we did not encounter organ perforation or significant bleeding. Furthermore, we did not observe post-operative intra-peritoneal infections, electrode migration or tissue erosion.

Changes in cardiovascular parameters such as modest decreases in heart rate and blood pressure appear to be consistent with the weight loss itself and no deleterious effects on cardiovascular risk factors were observed. Although the current sample size is small, the apparent lack of undesirable effects on blood pressure and heart rate are important to note since the vagus is a prominent regulator of parasympathetic tone on the cardiovascular system at the thoracic level. The intermittent vagal blockade is applied at the sub-diaphragmatic level. Experimental animal studies also show that there is no histological evidence of Wallerian degeneration or demyelination of the vagus after application of the electrical algorithm in the pig for at least 55 days. (data not shown) Moreover, application of the electrical signal for inhibition of vagal function (5 kHz for 5 minutes) has been shown to be rapidly reversible; thus, within 5 minutes of cessation of the inhibition algorithm, there is a recovery of >75% compound action potentials relative to baseline in both A$\delta$ and C fibers of the vagus nerve.

Vertical banded gastroplasty was performed either with (30 patients) or without (39 patients) truncal vagotomy on 69 morbidly obese patients with a mean BMI of 47 kg/m$^2$, (Kral J G, Gortz L, Hermansson G, Wallin G S. Gastroplasty for obesity: Long-term weight loss improved by vagotomy. World J Surg 1993; 17:75-9.) In patients followed for one year or longer, the vagotomy group had an average excess body weight loss (EWL) of 51% as compared to 34% for the non-vagotomy patients. In a separate long-term series of 21 patients, however, it was observed that initial weight loss was not maintained. (Groetz L, Kral J B. A five- to eight-year follow-up study of truncal vagotomy as a treatment for morbid obesity. Proceedings, Third Annual Meeting, American Society for Bariatric Surgery, Iowa City, Iowa, 18-20 Jun., 1986, p. 145) The effects of surgical vagotomy in preclinical studies in rodents suggest that, while there is inhibition of gastric accommodation for two weeks, the latter function was restored after continuous vagal interruption for four weeks. Takahashi T, Owyang C. Characterization of vagal pathways mediating gastric accommodation reflex in rats. J Physiol 1997; 504:479-88. The precise mechanism of this adaptation is unclear.

Based on the findings from this clinical trial, it can be concluded that intermittent, intra-abdominal vagal blocking using a novel, programmable medical device is associated with both significant excess weight loss and a desirable safety profile. Furthermore, study data support the therapeutic rationale of intermittent, intra-abdominal vagal blocking by documenting decreased hunger between meals and earlier satiation at meals, as well as an association between weight loss and vagal inhibition. In addition, a subset of patients shows a significant reduction of HbA1c at 4 weeks post treatment, suggesting an increase in glycemic control. These positive clinical results have led to the design and implementation of a randomized, double-blind, prospective, multi-center trial.

With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto. In addition, this disclosure contemplates application of a combination of electrical signal treatment by placement of electrodes on one or more nerves, one or more organs, and combinations thereof. This disclosure contemplates application of a therapy program to down regulate neural activity by application of electrical signal treatment by placement of electrodes on one or more nerves, one or more organs, and combinations thereof. This disclosure contemplates application of a therapy program to up regulate neural activity by application of electrical signal treatment by placement of electrodes on one or more nerves, one or more organs, and combinations thereof. This disclosure contemplates application of one or more therapy programs to down regulate and/or upregulate neural activity by application of electrical signal treatment by placement of electrodes on one or more nerves, one or more organs, and combinations thereof.

In the sections of this application pertaining to teachings of the prior art, the specification from prior art patents is substantially reproduced for ease of understanding the embodiment of the present invention. For the purpose of the present application, the accuracy of information in those patents is accepted without independent verification. Any publications referred to herein are hereby incorporated by reference.

What is claimed is:

1. A system for treating a patient with impaired glucose regulation comprising:
    at least two electrodes operably connected to an implantable pulse generator, wherein one of the electrodes is adapted to be placed on a vagus nerve below a vagal innervation of the heart;
    an implantable pulse generator that comprises a power module and a programmable therapy delivery module, wherein the programmable therapy delivery module is configured to deliver at least one therapy program comprising an electrical signal treatment applied intermittently multiple times in a day and over multiple days to the vagus nerve, wherein the electrical signal treatment is selected to reduce a HbA1C %, has a frequency selected to downregulate activity on the vagus nerve of at least 500 Hz, an on time and an off time, wherein the off time is selected to allow at least a partial recovery of the activity of the vagus nerve; and
    an external component comprising an antenna and a programmable storage and communication module, wherein programmable storage and communication module is configured to store the at least one therapy program and to communicate the at least one therapy program to the implantable pulse generator.

2. The system of claim 1, wherein the at least one electrode is adapted to be placed on an organ selected from the spleen, stomach, duodenum, pancreas and ileum.

3. The system of claim 1, wherein the at least one electrode is adapted to be placed on a second target nerve selected from a splanchnic nerve, a hepatic branch of the vagus nerve, a celiac branch of a vagus nerve and combinations thereof.

4. The system of claim 1, wherein the programmable therapy delivery module is configured to deliver an electrical signal having a frequency of at least 500 to 5000 Hz.

5. The system of claim 1, wherein the programmable therapy delivery module is configured to deliver an electrical signal having an on time of about 30 seconds to 5 minutes.

6. The system of claim 5, wherein the programmable therapy delivery module is configured to deliver an electrical signal having an off time of about 5 to 30 minutes.

7. The system of claim 1, wherein the programmable storage and communication module is configured to deliver a therapy program to the implantable pulse generator, wherein the program comprises an electrical signal treatment applied intermittently multiple times in a day and over multiple days, wherein the electrical signal treatment is selected to reduce a HbA1C %, has a frequency selected to down-regulate activity on the vagus nerve of at least 500 Hz, and has an on time and an off time, wherein the off time is selected to allow at least a partial recovery of the activity of the vagus nerve.

8. The system of claim 1, wherein the programmable storage and communication module is configured to store and communicate more than one therapy program, wherein each therapy program is different from one another, and is configured to be selected for communication.

9. The system of claim 1, wherein programmable therapy delivery module is configured to deliver a second therapy program comprising an electrical signal treatment applied intermittently multiple times in a day and over multiple days to a second target nerve or organ, wherein the electrical signal has a frequency selected to upregulate or down-regulate activity on the second target nerve or organ and has an on time and an off time, wherein the off time is selected to allow at least a partial recovery of the activity of the second target nerve or organ to baseline levels.

10. The system of claim 9, wherein the second target nerve is the splanchnic nerve or the celiac branch of the vagus nerve.

11. The system of claim 9, wherein the second target organ is the duodenum or ileum.

12. The system of claim 1, further comprising a sensor operable connected to the implantable pulse generator.

13. The system of claim 12, wherein the sensor detects an increase or decrease of blood glucose from a threshold level.

14. The system of claim 12, wherein the programmable therapy delivery module is configured to deliver the second therapy program in response to a signal from the sensor.

15. The system of claim 9, wherein the upregulating signal has a frequency of less than 200 Hz.

16. The system of claim 15, wherein the on time is about 30 seconds to 15 minutes.

17. The system of claim 15, wherein the off time is about 5 to 45 minutes.

18. A method of treating a condition associated with impaired glucose regulation in a subject comprising:
    Treating the subject by applying an intermittent electrical signal to a vagus nerve below a vagal innervation of the heart of the subject having impaired glucose regulation using the system of claim 1, with said electrical signal treatment selected to reduce a HbA1C %, and selected to down-regulate neural activity on the vagus nerve with a frequency of at least 500 Hz, and to restore neural activity on the vagus nerve upon discontinuance of said signal.

19. The method according to claim 18, wherein the condition is type 2 diabetes.

20. The method of claim 18, wherein the electrical signal is applied intermittently in a cycle including an on time of application of the signal followed by an off time during which the signal is not applied to the nerve, wherein the on and off times are applied multiple times per day over multiple days.

21. The method of claim 20, wherein the on time is selected to have a duration of about 30 seconds up to about 5 minutes.

22. The method according to claim 18, wherein the electrical signal is applied at a frequency of about 500 Hz to 5000 Hz.

23. The method according to claim 18, wherein the electrical signal is applied on the hepatic branch of the vagus nerve.

24. The method according to claim 18, wherein the electrical signal is applied on the celiac branch of the vagus nerve.

25. The method according to claim 18, wherein the electrical signal is applied to the liver, duodenum, jejunum, ileum, or combinations thereof.

26. The method of claim 18, further comprising applying an upregulating signal to a second target nerve or organ.

27. The method of claim 26, wherein the downregulating and upregulating signals are applied at the same time or different time.

28. The method of claim 26, wherein the second target nerve is the splanchnic nerve.

29. The method of claim 26, wherein the second target organ is the duodenum or ileum.

30. The method according to claim 18, further comprising administering an agent that improves glucose control.

31. The method of claim 30, wherein the agent increases the amount of insulin and/or increases the sensitivity of cells to insulin.

32. The method of claim 31, wherein the agent that increases the amount of insulin is selected from the group consisting of insulin, insulin analogs, sulfonylureas, meglitinides, GLP-1 analogs, and DPP4 inhibitors.

33. The method of claim 31, wherein the agent that increases the sensitivity of cells to insulin is a PPAR alpha, gamma, or delta agonist.

34. A diabetes or prediabetes treatment comprising:
   i) selecting a drug for treating diabetes or impaired glucose control for a patient where effective dosages for treating diabetes or prediabetes for such a patient are associated with disagreeable side effects or impaired glycemic control; and
   ii) treating a patient for diabetes or impaired glucose control with a concurrent treatment comprising:
   a) applying an intermittent electrical signal treatment using a system of claim 1 to a vagus nerve below a vagal innervation of the heart of the patient at multiple times per day and over multiple days, wherein the electrical signal treatment is selected to reduce a HbA1C %, and selected to down-regulate afferent and efferent neural activity on the vagus nerve with a frequency of at least 500 Hz, and with neural activity restoring upon discontinuance of said block; and
   b) administering said drug to the patient.

35. A method of making a system for treating a patient with impaired glucose regulation comprising:
   providing at least two electrodes operably connectable to an implantable pulse generator, wherein one of the electrodes is adapted to be placed on a vagus nerve below a vagal innervation of the heart;
   configuring a programmable therapy delivery module of the implantable pulse generator to deliver at least one therapy program comprising an electrical signal treatment applied intermittently multiple times in a day and over multiple days to the vagus nerve, wherein the electrical signal treatment is selected to reduce a HbA1C %, has a frequency selected to downregulate activity on the vagus nerve of at least 500 Hz, and has an on time and an off time, wherein the off time is selected to allow at least a partial recovery of the activity of the vagus nerve; and
   configuring a programmable storage and communication module of an external component to store the at least one therapy program and to communicate the at least one therapy program to the implantable pulse generator.

36. The method of claim 35, further comprising
   configuring the programmable therapy delivery module of the implantable pulse generator to deliver the second therapy program comprising an electrical signal treatment applied intermittently multiple times in a day and over multiple days to a second target nerve or organ, wherein the electrical signal has a frequency selected to upregulate or down-regulate activity on the second target nerve or organ and has an on time and an off time, wherein the off time is selected to allow at least a partial recovery of the activity of the second target nerve or organ to baseline levels.

37. The method of claim 35, further comprising providing a sensor to the implantable pulse generator.

38. The method of claim 35, further comprising configuring the programmable therapy delivery module of the implantable pulse generator to deliver the second therapy program upon a signal from the sensor.

\* \* \* \* \*